(12) United States Patent
Van Wyk et al.

(10) Patent No.: US 8,790,340 B2
(45) Date of Patent: Jul. 29, 2014

(54) ELECTROSURGICAL DEVICE HAVING FLOATING-POTENTIAL ELECTRODE FOR OBSTRUCTION REMOVAL

(75) Inventors: Robert A. Van Wyk, St. Pete Beach, FL (US); Yuval Carmel, Rockville, MD (US); Anatoly Shkvarunets, Rockville, MD (US)

(73) Assignee: ElectroMedical Associates, LLC, Bethesda, MD (US)

( * ) Notice: Subject to any disclaimer, the term of this patent is extended or adjusted under 35 U.S.C. 154(b) by 112 days.

(21) Appl. No.: 13/493,975

(22) Filed: Jun. 11, 2012

(65) Prior Publication Data

US 2012/0245578 A1    Sep. 27, 2012

Related U.S. Application Data

(62) Division of application No. 13/451,138, filed on Apr. 19, 2012, now Pat. No. 8,348,944, which is a division of application No. 11/859,297, filed on Sep. 21, 2007, now Pat. No. 8,177,784.

(51) Int. Cl.
   *A61B 18/18* (2006.01)
(52) U.S. Cl.
   USPC ............................. 606/41; 606/45; 606/49
(58) Field of Classification Search
   USPC ............................. 606/48, 41, 45–46, 49–52
   See application file for complete search history.

(56) References Cited

U.S. PATENT DOCUMENTS

| | | |
|---|---|---|
| 2,448,741 A | 9/1948 | Scott et al. |
| 3,856,015 A | 12/1974 | Iglesias |
| 3,901,242 A | 8/1975 | Storz |
| 4,674,499 A | 6/1987 | Pao |
| 4,682,596 A | 7/1987 | Bales |
| 4,726,370 A | 2/1988 | Karasawa |
| 4,917,082 A | 4/1990 | Grossi et al. |
| 5,195,959 A | 3/1993 | Smith |
| 5,277,696 A | 1/1994 | Hagen |
| 5,314,459 A | 5/1994 | Swanson |
| 5,486,173 A | 1/1996 | Vancaillie |
| 5,582,610 A | 12/1996 | Grossi et al. |
| 6,033,400 A | 3/2000 | Grossi et al. |
| 6,066,134 A | 5/2000 | Eggers |
| 6,113,597 A | 9/2000 | Eggers et al. |
| 6,169,296 B1 | 1/2001 | Kamiyama et al. |
| 6,197,025 B1 | 3/2001 | Grossi et al. |
| 6,277,114 B1 | 8/2001 | Bullivant et al. |
| 6,391,025 B1 | 5/2002 | Weinstein et al. |
| 6,419,684 B1 | 7/2002 | Heisler et al. |
| 6,565,560 B1 | 5/2003 | Goble et al. |
| 6,575,968 B1 | 6/2003 | Eggers |
| 6,796,982 B2 | 9/2004 | Carmel et al. |

(Continued)

FOREIGN PATENT DOCUMENTS

| | | |
|---|---|---|
| GB | 2324274 | 12/1997 |
| WO | WO 03/075777 | 9/2003 |

*Primary Examiner* — Jaymi Della
(74) *Attorney, Agent, or Firm* — Chalin A. Smith; Smith Patent

(57) ABSTRACT

Disclosed herein are embodiments of an electrosurgical device that include one or more floating electrodes and are specifically adapted to remove, cut, resect, ablate, vaporize, denaturize, drill, coagulate and form lesions in soft tissues, with or without externally supplied liquids, preferably in combination with a resectoscope, particularly in the context of urological, gynecological, laparoscopic, arthroscopic, and ENT procedures. Specific adaptations for urological and gynecological applications, for example kidney stone removal and BPH treatment, are also described.

9 Claims, 33 Drawing Sheets

(56) References Cited

U.S. PATENT DOCUMENTS

| | | |
|---|---|---|
| 6,840,937 B2 | 1/2005 | Van Wyk |
| 6,899,712 B2 | 5/2005 | Moustafis et al. |
| 6,921,398 B2 | 7/2005 | Carmel et al. |
| 6,921,399 B2 | 7/2005 | Carmel et al. |
| 6,955,676 B2 | 10/2005 | Quick |
| 7,166,103 B2 | 1/2007 | Carmel et al. |
| 2002/0038122 A1 | 3/2002 | Peters et al. |
| 2003/0120269 A1 | 6/2003 | Bessette et al. |
| 2003/0176873 A1* | 9/2003 | Chernenko et al. ........... 606/127 |
| 2004/0030330 A1 | 2/2004 | Brassell et al. |
| 2004/0049183 A1 | 3/2004 | Ellman et al. |
| 2004/0193150 A1 | 9/2004 | Sharkey et al. |
| 2005/0065510 A1 | 3/2005 | Carmel et al. |
| 2005/0234446 A1 | 10/2005 | Van Wyk et al. |
| 2005/0277915 A1 | 12/2005 | DeCesare et al. |
| 2006/0259031 A1 | 11/2006 | Carmel et al. |
| 2006/0293653 A1 | 12/2006 | Van Wyk |
| 2008/0077129 A1 | 3/2008 | Van Wyk et al. |
| 2009/0125021 A1 | 5/2009 | Brommersma |

\* cited by examiner

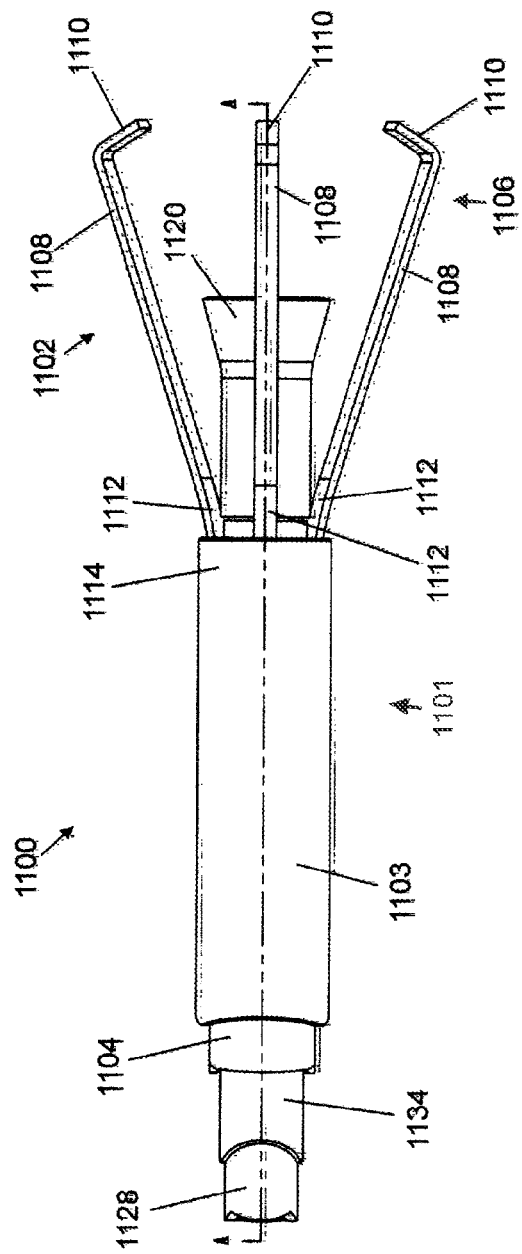
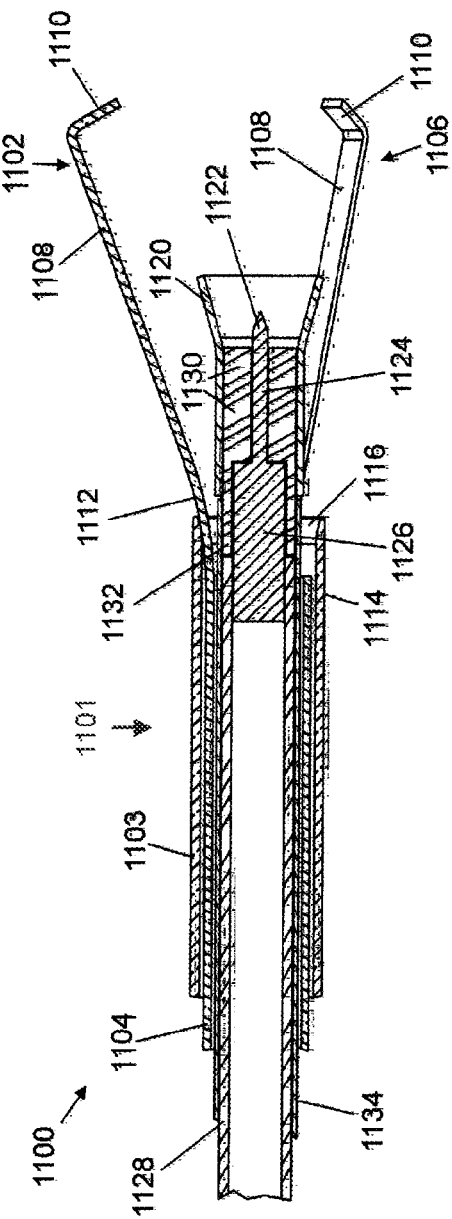
Fig. 41
Fig. 42

ELECTROSURGICAL DEVICE HAVING FLOATING-POTENTIAL ELECTRODE FOR OBSTRUCTION REMOVAL

PRIORITY

This application is a divisional of U.S. patent application Ser. No. 13/451,138 filed Apr. 19, 2012, now U.S. Pat. No. 8,348,944 issued Jan. 8, 2013, which, in turn, is a divisional of U.S. patent application Ser. No. 11/859,297 filed Sep. 21, 2007, now U.S. Pat. No. 8,177,784 issued May 15, 2012, the entire contents of which are incorporated by reference herein.

FIELD OF THE INVENTION

The present invention relates generally to the field of electrosurgery, and more particularly, to high efficiency electrosurgical devices and methods which use radio frequency (RF) energy to cut, resect, ablate, vaporize, denaturize, drill, energy coagulate and form lesions in soft tissues, with or without externally supplied liquids. The electrosurgical devices of the instant invention find particular utility in combination with a resectoscope, in the context of urological, gynecological, laparoscopic, arthroscopic, and ENT procedures.

BACKGROUND OF THE INVENTION

As compared to conventional tissue removal techniques, electrosurgical procedures are advantageous in that they generally reduce patient bleeding and trauma. More recently, electrosurgical devices have gained significant popularity due to their ability to accomplish outcomes with reduced patient pain and accelerated return of the patient to normal activities. Such instruments are electrically energized, typically using an RF generator operating at a frequency between 100 kHz to over 4 MHz.

Many types of electrosurgical devices are currently in use. They can be divided to two general categories—monopolar devices and bipolar devices. When monopolar electrosurgical devices are used, the RF current generally flows from an exposed active electrode, through the patient's body, to a passive, return current electrode that is externally attached to a suitable location on the patient body. In this manner, the patient's body becomes part of the return current circuit. In the context of bipolar electrosurgical devices, both the active and the return current electrodes are exposed, and are typically positioned in close proximity to each other, preferably mounted on the same instrument. In bipolar procedures, the RF current flows from the active electrode to the return electrode through the nearby tissue and conductive fluids.

High frequency electrosurgical instruments, both monopolar and bipolar, have been used in the context of many surgical procedures in such fields as urology, gynecology, laparoscopy, general surgery, arthroscopy, ear nose and throat and more. In many fields of electrosurgery, monopolar and bipolar instruments operate according to the same principles. For example, the electrosurgical interventional instrument, whether monopolar or bipolar, may be introduced through a cannula, a resectoscope, or alternatively directly to perform the needed surgical procedure in the target area of the patient's body. In some cases, an externally supplied liquid (often referred to as an "irrigant"), either electrically conductive or non-conductive, is applied. In other electrosurgical procedures, the instruments rely only on locally available bodily fluids, without requiring an external source of fluid. Procedures performed in this manner are often referred to as performed in "dry-field". When necessary, the electrosurgical instruments may be equipped with irrigation, aspiration or both.

Even though the benefits are well recognized, current electrosurgical instruments and procedures suffer from very significant deficiencies. For example, monopolar devices require the use of an additional external component, namely one or more grounding plates, remotely attached to a suitable location on the skin of the patient. Thus, in that monopolar devices require current to flow from the active electrode through the patient's body, they invariably allow for the possibility that some of the current will flow through undefined paths in the patient's body, particularly when the instrument is not properly designed and positioned.

Bipolar electrosurgical devices have their own inherent drawbacks, often resulting from the close orientation of the return and active electrodes. The return electrode necessarily has a small area and, as a result, can cause undesired tissue heating, coagulating or evaporation at its contact point with the patient's tissue due to the relatively high current densities present thereon. In addition, with the bipolar configuration, the close proximity of the active and return electrodes creates the danger that the current will short across the electrodes. For this reason, bipolar devices normally operate at relatively low voltage (typically 100 to 500 V) to decrease the chances that a spark will bridge the gap between the active and return electrodes.

Electrosurgical procedures which cut or vaporize tissue rely on generation of sparks in the vicinity of the active electrodes to vaporize the tissue. Sparking is often referred to as "arcing" within gaseous bubbles in liquid, or alternatively as plasmas. Operation at relatively low voltage, as is necessary with bipolar instruments, leads to less efficient sparking, reduced efficiency of the instrument, undesirable overheating of nearby tissue, and longer procedure time. Moreover, the use of electrosurgical bipolar procedures in electrically conductive environments is inherently problematic. For example, many arthroscopic procedures require flushing of the region to be treated with saline, both to maintain an isotonic environment, to carry away process heat and debris, and to keep the field of view clear. The presence of saline, which is a highly conductive electrolyte, can also cause electrical shorting of a bipolar electrosurgical probe, thereby causing probe destruction and unintended and unnecessary heating in the treatment environment which, in turn, can result in unintended and uncontrolled tissue destruction.

In addition, current monopolar and bipolar instruments used to cut or vaporize tissue often do not have effective means for controlling bubbles, which is essential to the safety and efficiency of many procedures. As a result, the efficiency of the instruments is often low and the procedure length is increased. Electrosurgical instruments that lack an effective means for trapping of bubbles include, for example, cutting loops, rollers, needles and knives, resection instruments and ablators. Furthermore, many current monopolar and bipolar instruments are not designed to take full advantage of either the electrical properties of the fluids present in the vicinity of the procedure site (bodily fluids, including blood, as well as irrigation fluids, either electrically conductive or non-conductive) or the electrical properties of the tissue itself.

Vaporizing electrodes (ablators) currently available for use in conductive liquids, whether monopolar or bipolar, have an active electrode surrounded by an insulator that is significantly larger in size than the ablating surface of the electrode. For ablators with a circular geometry, the diameter of the portion of the probe which generates ablative arcs (i.e., the "working" diameter) is generally not greater than 70 to 80 percent of the diameter of the insulator (i.e., the "physical" diameter). Accordingly, only about 50% of the physical probe area can be considered effective. This increases the size of the distal end of the electrode necessary to achieve a given ablative surface size, and necessitates the use of cannulae, often with unnecessarily large lumens, an undesirable condition.

As noted above, it is well known in the prior art to use high frequency current in electrosurgical instruments, both monopolar and bipolar, introduced via a cannula, resectoscope, endoscope or directly, to perform the desired surgical procedure in such fields as urology, gynecology, laparoscopy, general surgery, arthroscopy, ear nose and throat and more. In fact, a number of radio frequency devices, both monopolar and bipolar, and techniques, both in conductive and non-conductive fluids, are described in the art for urological and gynecological purposes. Illustrative examples include: Alschibaja et al. [(2006) *BJU Int.* 97(2):243-6]; Botto [(2001) J. of Endourology, 15 (3) 313-316]; and Keoghane (pinpointmedical.com/urology) as well as U.S. Pat. No. 3,856,015 (Iglesias), U.S. Pat. No. 3,901,242 (Storz), and U.S. Pat. No. 2,448,741 (Scott et al.), which illustrate prior art cutting electrode assemblies for urology, gynecology and endoscopy. Other examples include: Smith (U.S. Pat. No. 5,195,959) and Pao (U.S. Pat. No. 4,674,499), which describe monopolar and bipolar electrosurgical devices, respectively, that include irrigation channels. Finally, Eggers et al. (U.S. Pat. No. 6,113, 597) describes bipolar instruments for resecting and/or ablating tissue within the urethra, prostate and bladder.

Endoscopic transurethral resection and/or thermal treatment of tissue is generally accomplished using a resectoscope, a device which allows the scope and other instruments to pass easily into the urethra. Resectoscopes are well known in the art. For example, in U.S. Pat. No. 4,726,370, Karasawa et al. describe a conventional resectoscope device and electrodes suited for use therewith. Various elongated probes are used to cut, vaporize, coagulate, or otherwise thermally treat tissue. Additional electrosurgical probes for use with a resectoscope are disclosed by Grossi et al. in U.S. Pat. Nos. 4,917, 082, 6,033,400, and 6,197,025. Resectoscopes, along with their associated electrosurgical probes, are also used in various laparoscopic and gynecological procedures.

Endoscopic electrosurgical probes of the type used with a resectoscope may be used with conductive or nonconductive irrigants. When conductive irrigants are used, current flows and/or arcing from any uninsulated portion of the active electrode which contacts the conductive fluid. Due to this reality, probes for use in conductive fluids must be insulated except for portions which will give the desired clinical effect during use. In a nonconductive fluid environment, conduction occurs only from portions of the active electrode which are in sufficiently close proximity to tissue to cause current flows and/or arcing between the electrode and the tissue, or from portions of the electrode which are in contact with tissue. During a surgical procedure, however, even non-conductive irrigants can achieve some level of conductivity, for example as a result of bodily fluids seeping from the patient's tissue into the irrigant. This contamination may increase the local conductivity to a degree sufficient to cause significant current flow from uninsulated portions of a probe designed for use in a non-conductive irrigant. Accordingly, it may be presumed that all fluids have some level of conductivity during laparoscopic electrosurgery, and that all probes which are used partially or completely submerged in a liquid will benefit from a construction that maximizes electrode efficiency by maximizing the portion of the RF energy which provides clinical benefit.

Probes may be used for vaporization or for thermal modification, such as lesion formation. Vaporization occurs when the current density at the active electrode is sufficient to cause localized boiling of the fluid at the active electrode, and arcing within the bubbles formed. When the current density is insufficient to cause boiling, the tissue in proximity to the active electrode is exposed to high-temperature liquid and high current density. The temperature of the liquid and tissue is affected by the current density at the active electrode, and the flow of fluid in proximity to the electrode. The current density is determined by the probe design and by the power applied to the probe. Any given probe, therefore, can function as either a vaporizing probe or a thermal treatment probe, depending on the choice of the power applied to the probe. Lower powers will cause a probe to operate in a thermal treatment mode rather than in the vaporizing mode possible if higher power is applied.

The bubbles which form at the active electrode when a probe is used in vaporizing mode, form first in regions of the highest current density and lowest convection of the liquid. When they reach a critical size, these bubbles support arcing within and allow for vaporization of tissue. Bubbles also form in areas of lower current density as the conductive liquid in these regions reaches sufficient temperature. While these bubbles generally do not support arcing, they cover portions of the exposed electrode surface, thereby insulating these portions of the surface. This insulation of non-productive regions of the electrode decreases non-beneficial current flow into the liquid thereby allowing the electrode to achieve its clinically beneficial results at lower power levels. It is possible to increase electrode efficiency by managing these bubbles so as to retain them in regions in which their presence insulates the electrode.

In summary, the geometry, shape and materials used for the design and construction of electrosurgical instruments greatly affect the performance. Electrodes with inefficient designs will require substantially higher power levels than those with efficient designs. While currently available electrodes are capable of achieving desired surgical effects, they are not efficient for accomplishing these tasks and may result in undesired side effects to the patient.

SUMMARY OF THE INVENTION

In view of the everpresent need in the art for more efficient electrode design, it is accordingly an object of the present invention to provide an electrosurgical device which has high efficiency.

It is also an object of the present invention to provide an electrosurgical device which may be readily used in combination with a resectoscope It is further an object of the present invention to provide an electrosurgical device which may be used in applications in which the target tissue is not submerged in a liquid environment.

It is additionally an object of the present invention to provide an electrosurgical device capable of operating in electrically conductive and non-conductive fluid environments, as well as in dry fields (bodily fluids).

These and other objects are accomplished in the invention herein disclosed, which is directed to an advanced, high efficiency, electrosurgical device designed for use with a resectoscope, and equipped with one or more additional metallic electrodes which are not connected directly to any part of power supply circuit. This disconnected electrode may contact the surrounding conducting liquid and/or tissue. The electrical potential of this disconnected electrode is "floating"

and is determined by the size and position of the electrode, the tissue type and properties, and the presence or absence of bodily fluids or externally supplied fluid. "Floating" electrodes for electrosurgery are described in co-pending U.S. patent application Ser. No. 10/911,309 (published as US 2005-0065510) and Ser. No. 11/136,514 (published as US 2005-023446), the contents of which are incorporated by reference herein in their entirety. In the context of the present invention, the "floating" electrode is preferably mounted in such a way that one portion of the electrode is in close proximity to the tip of the active electrode, in the region of high potential. Another portion of the floating electrode is preferably placed farther away, in a region of otherwise low potential. This region of low potential may be in contact with the fluid environment, in contact with tissue, or both.

In the context of the present invention, the floating electrode generates and concentrates high power density in the vicinity of the active region, and results in more efficient liquid heating, steam bubble formation and bubble trapping in this region. This increases the probe efficiency, which, in turn, allows the surgeon to substantially decrease the applied RF power and thereby reduce the likelihood of patient burns and unintended local tissue injury. The probe may be operated so that the portion of the floating electrode in close proximity to the active electrode has sufficient current density to produce vaporization of the liquid and arcing so as to vaporize tissue. Alternatively, the probe may be operated so that the floating electrode contacts tissue, wherein those portions of the floating electrode in contact with the tissue have sufficient current density to thermally coagulate blood vessels and tissue. This is particularly useful for achieving hemostasis in vascular tissue, such as, for instance, that present when performing tonsillectomies.

The innovative electrosurgical devices with floating electrodes of the present invention may be very effective in other medical procedures, other than those involving tissue evaporation (ablation), including, for instance, for thermal tissue treatment, lesion formation, tissue sculpting, tissue "drilling", and coagulation with or without externally supplied liquids.

Accordingly, in view of these noted needs and objectives, the present invention provides in one embodiment an electrosurgical instrument comprising:
 (a) an elongate shaft having a proximal end configured for connection to an electrosurgical power source and a distal end having an electrode assembly mounted thereto;
 (b) a conductive member coupled to the elongate shaft and extending between the proximal and distal ends thereof; and
 (c) an electrode assembly having an active surface that forms an acute angle with the longitudinal axis of the shaft and comprises conductive active and floating electrodes positioned in close proximity to each other and separated by a non-conductive dielectric insulator;
 wherein the active surface includes a continuous or discontinuous array of raised and recessed portions that creates regions of high current density for high efficiency vaporization of tissue.

In another preferred embodiment, the present invention provides an electrosurgical instrument as described above, with the exception that the electrode assembly has a layered construction (referred to as a sandwich construction) comprised of (i) an active electrode having upper and lower surfaces; (ii) an insulator having upper and lower surfaces, wherein the upper surface of the insulator is adhered to the lower surface of the active electrode; and (iii) a floating electrode having upper and lower surfaces, wherein the upper surface of the floating electrode adhered to the lower surface of the insulator.

In a further preferred embodiment, the present invention provides an electrosurgical instrument as described above, with the exception that the electrode assembly comprises an active electrode, a floating electrode, and an insulator separating the active and floating electrodes, wherein the insulator is concentrically disposed about the active electrode, and the floating electrode is concentrically disposed about the insulator;

In the context of the present invention, the electrosurgical device herein disclosed may take the form of a probe for use with a resectoscope, wherein the probe has an elongated proximal portion and an active distal portion, the distal portion having at its distal end at least one active electrode and at least one floating electrode. The active electrode is preferably connected via cabling disposed within the elongated proximal portion to an externally disposed electrosurgical generator. At least a portion of the distal-most portion of at least one floating electrode should be positioned in close proximity to at least one active electrode. In a preferred embodiment, the active electrode has an ablating surface (often referred to herein as the "active surface" or "working surface") composed of an array of raised and recessed regions particularly configured to maximize bubble retention and concentrate power density. The array may take the form of, for example, a plurality of walls and grooves, a plurality of elevated pins, a plurality of bumps and pockets, or a combination thereof. So long as the array performs the desired function (e.g., bubble retention, power density concentration), the specific design, geometry, arrangement and configuration of the array or its components is not particularly limited. For example, the array be continuous or discontinuous, evenly or unevenly spaced, composed of raises and recesses that are linear or non-linear (e.g., curvilinear, wavy, zigzagged, angled, etc.), parallel or circumferential positioned, or the like. In one particularly preferred embodiment, the array is composed of a plurality of grooves etched into the ablating surface of the active electrode, such grooves being of a depth and width for maximal retention of bubbles within the grooves.

The floating electrode preferably surrounds the active electrode and is separated therefrom by a dielectric member. The floating electrode intensifies the electric field in proximity to the active electrode and aids bubble retention when the probe is used to vaporize tissue. In other embodiments, the probe has irrigation supplied to the probe tip. In still other embodiments, the active electrode has a plurality of protuberances formed on its ablating surface. These electrodes may be used for vaporizing tissue by applying sufficient voltage for bubble formation and arcing, or may be used for thermal treatment of tissue by applying lower voltages.

Other embodiments include small-diameter, elongated active electrodes having distal ends forming spherical radii, cylindrical radii, conical points or other shapes.

In another embodiment, the device may be configured exclusively for thermal treatment by providing an active electrode with a hemispherical shape.

In still other embodiments, a shaped wire electrode may be used to resect rather than vaporize tissue from a body. In this manner, the electrode functions as a cutting instrument. An illustrative embodiment of such an electrosurgical instrument may comprise:
 (a) an elongate shaft having a proximal end configured for connection to an electrosurgical power source and a distal end having an electrode assembly mounted thereto;

(b) a conductive member coupled to the elongate shaft and extending between the proximal and distal ends thereof;
(c) first and second laterally opposed, distally extending, insulated conductive members mounted to the distal end of the shaft;
(d) a pair of floating electrodes, one concentrically disposed about the distal end of the first conductive member and the other concentrically disposed about the distal end of the second of conductive member;
(e) a bubble trap mounted to the distal ends of the first and second conductive members; and
(f) an active loop electrode mounted to the bubble trap, extending between the first and second conductive members;
   wherein the bubble trap is formed from a nonconductive dielectric material while the active loop and floating electrodes are formed from an electrically conductive material;
   further wherein the at least one active electrode is electrically connected to the conductive member while the at least one floating electrode is not connected to either the conductive member or the electrosurgical power source.

In another embodiment, the device may be configured for the treatment of kidney stones.

The present invention also provides electrosurgical methods which utilize radio frequency (RF) energy to cut, resect, ablate, vaporize, denaturize, drill, coagulate and form lesions in soft tissues, with or without externally supplied liquids, for example, in the context of urological, gynecological, laparoscopic, arthroscopic, and ENT procedures. In an illustrative embodiment, the present invention provides a method of treating benign prostatic hyperplasia (BPH) in a subject in need thereof, comprising the steps of:
(a) inserting a resectoscope outer sheath into the urethra of a subject;
(b) advancing the resectoscope outer sheath until the distal end is adjacent a target site of the prostate of the subject;
(c) advancing a resectoscope working element with telescope and an electrosurgical instrument of the present invention through the resectoscope outer sheath to the target site;
(d) introducing an irrigant to the target site so as to submerge the active and floating electrodes of the electrosurgical instrument; and
(e) applying current to the active electrode of the electrosurgical instrument and moving the electrosurgical instrument in a proximal direction relative to the prostate tissue;
wherein step (e) results in vaporization, thermal modification and hemostatic dessication of adjacent prostate tissue.

These and other objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention.

BRIEF DESCRIPTION OF THE FIGURES

FIG. 41 is a plan view of the distal portion of an alternate embodiment for removal of kidney stones.
FIG. 42 is a side elevational sectional view of the objects of FIG. 41 at location A-A of location 41.

FIG. 51a is a side elevational view of the objects of FIG. 50a.

FIG. 52 is a distal axial view of the objects of FIG. 50a.

FIG. 53 is a perspective view of the objects of FIG. 50a.

FIG. 54 is a proximal axial view of the objects of FIG. 50a.

FIG. 55 is an exploded view of the objects of FIG. 50a.

DETAILED DESCRIPTION OF THE PREFERRED EMBODIMENTS

Figure 1:
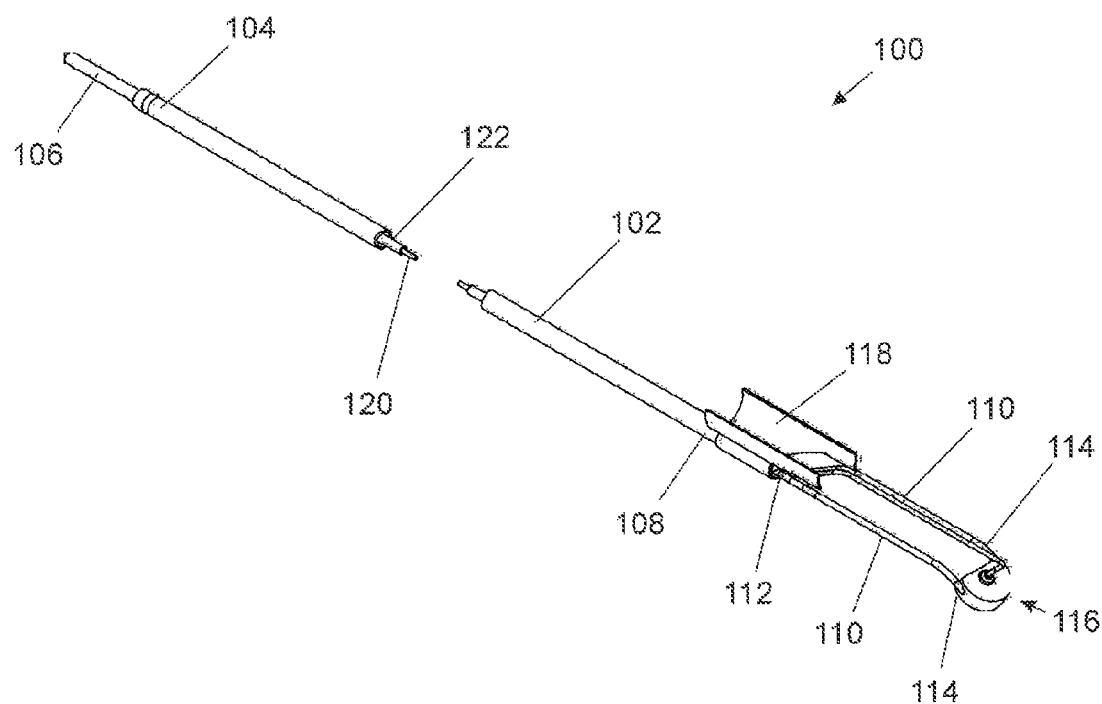
FIG. 1 is a perspective view of an electrosurgical probe constructed in accordance with the principles of this invention.
Figure 2:
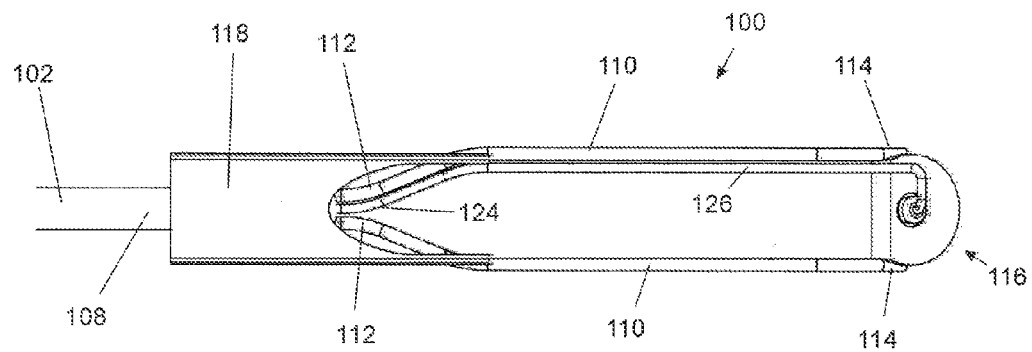
FIG. 2 is an expanded plan view of the distal portion of the object of FIG. 1.
Figure 3:
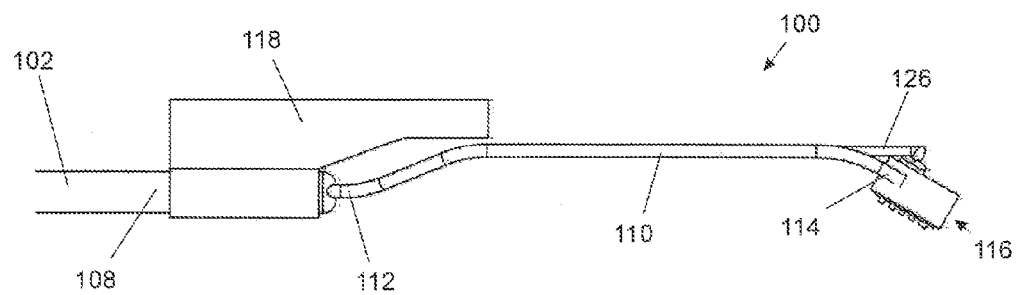
FIG. 3 is a side elevational view of the objects of FIG. 2.
Figure 4:
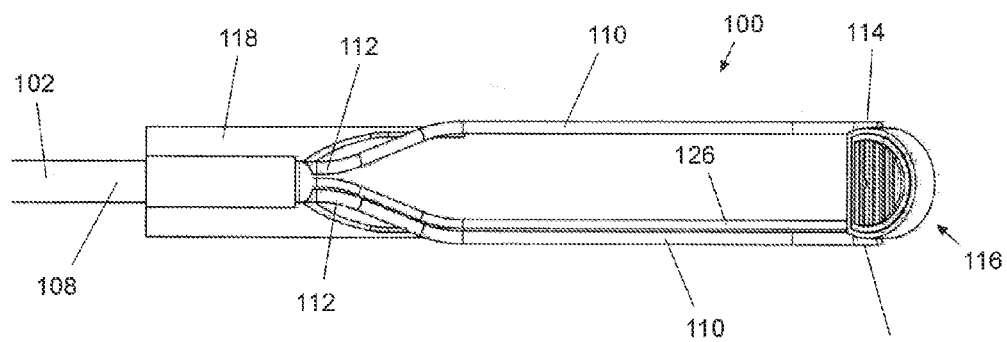
FIG. 4 is a bottom side plan view of the objects of FIG. 2.
Figure 5:
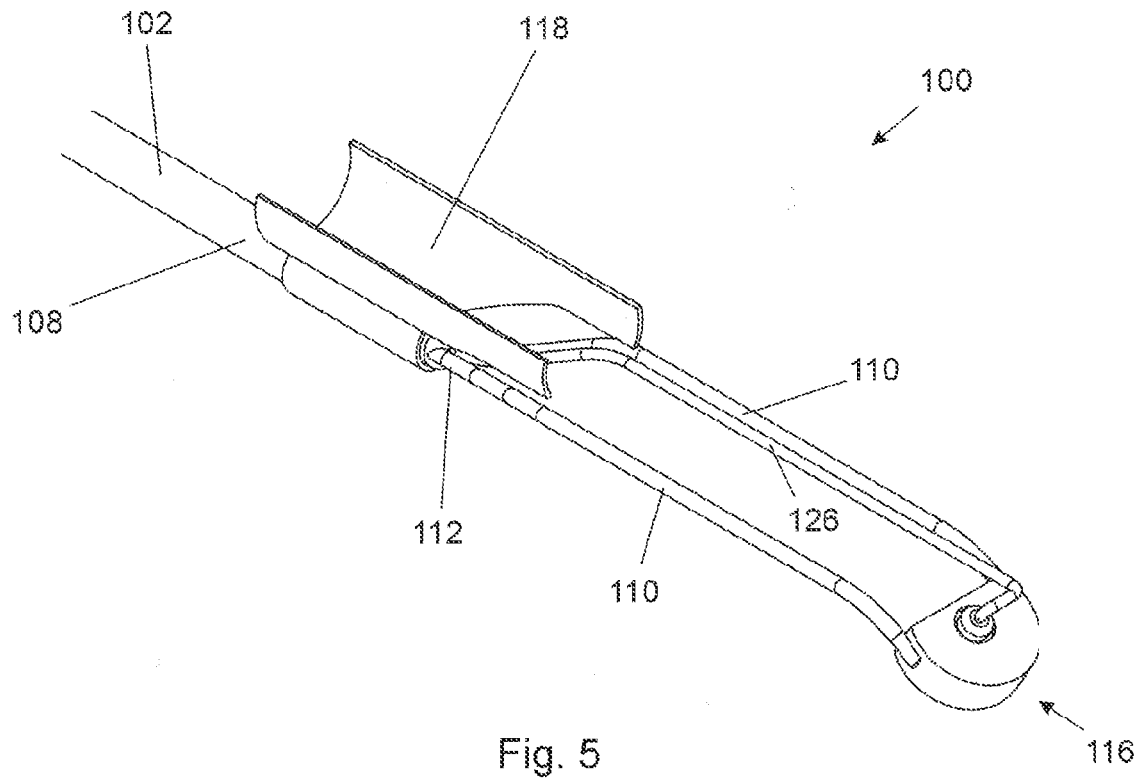
FIG. 5 is an expanded perspective view of the distal portion of the objects of FIG. 1.
Figure 6:
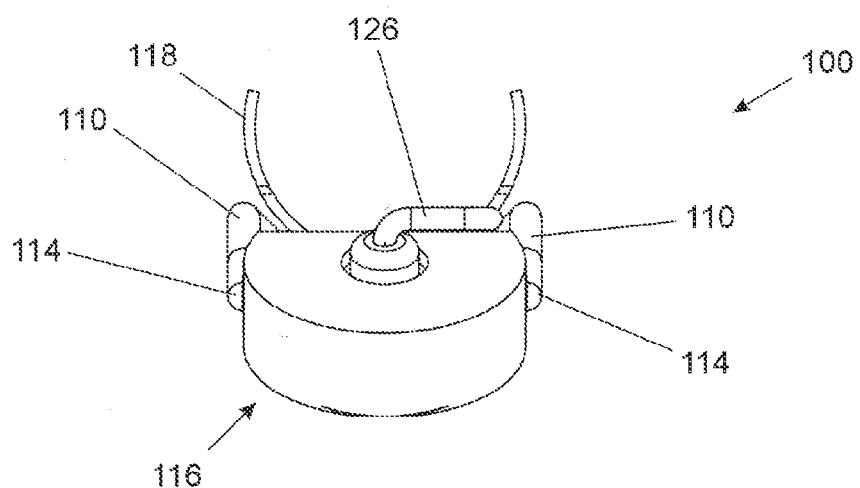
FIG. 6 is an expanded distal axial view of the objects of FIG. 1.
Figure 7:
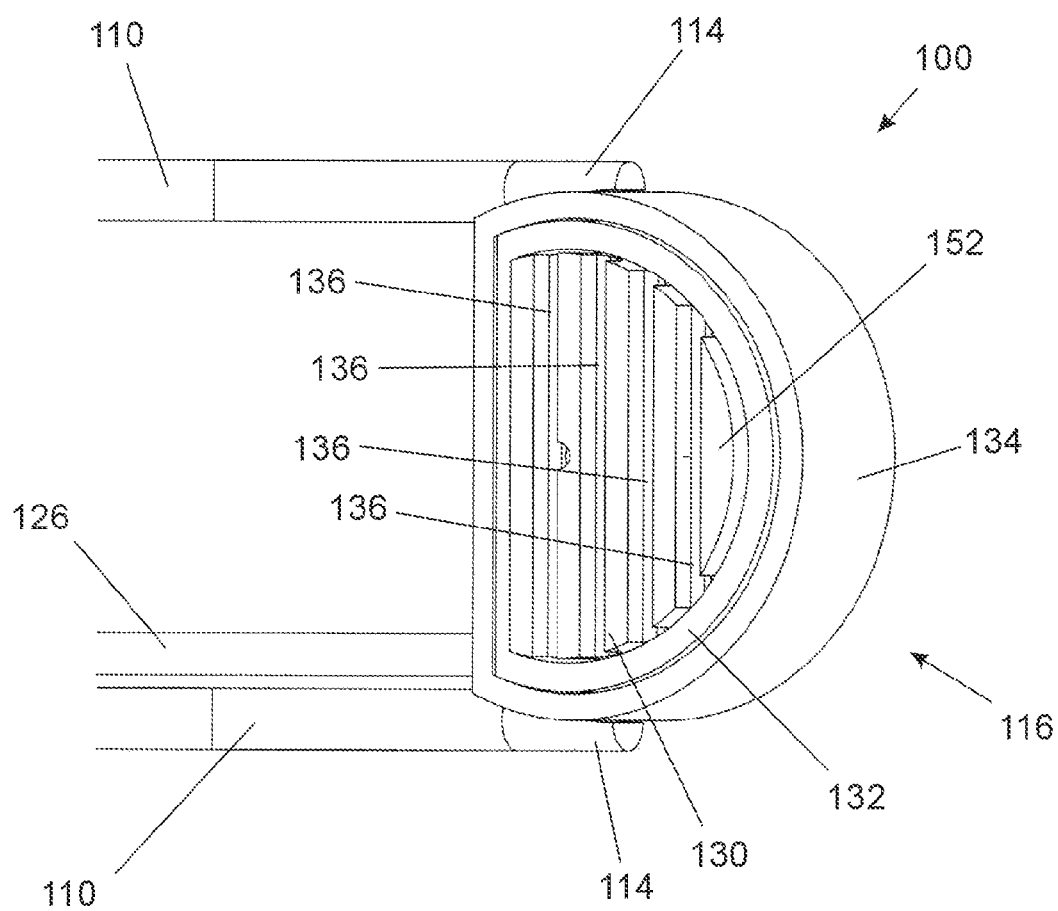
FIG. 7 is an expanded bottom side plan view of the distal-most portion of the objects of FIG. 2.

In the context of the present invention, the following definitions apply:

The words "a", "an", and "the" as used herein mean "at least one" unless otherwise specifically indicated.

In common terminology and as used herein, the term "electrode" may refer to one or more components of an electrosurgical device (such as an active electrode or a return electrode) or to the entire device, as in an "ablator electrode" or "cutting electrode". Such electrosurgical devices are often interchangeably referred to herein as "probes" or "instruments".

The term "proximal" refers to that end or portion which is situated closest to the user; in other words, the proximal end of the electrosurgical device of the instant invention will typically comprise the handle portion.

The term "distal" refers to that end or portion situated farthest away from the user; in other words, the distal end of the electrosurgical device of the instant invention will typically comprise the active electrode portion.

The instant invention has both human medical and veterinary applications. Accordingly, the terms "subject" and "patient" are used interchangeably herein to refer to the person or animal being treated or examined. Exemplary animals include house pets, farm animals, and zoo animals. In a preferred embodiment, the subject is a mammal.

Unless otherwise defined, all technical and scientific terms used herein have the same meaning as commonly understood by one of ordinary skill in the art to which this invention belongs. In case of conflict, the present specification, including definitions, will control.

As noted above, the present invention is directed to high efficiency monopolar or bipolar electrosurgical devices and methods which utilize radio frequency (RF) energy to cut, resect, ablate, vaporize, denaturize, drill, coagulate and form lesions in soft tissues, with or without externally supplied liquids, having particular utility in the context of urological, gynecological, laparoscopic, arthroscopic, and ENT procedures. At its most basic, the device of the present invention is comprised of electrosurgical probe having a metallic electrode coated entirely with dielectric, with the exception of an exposed portion located at the electrode tip. This exposed tip is referred to herein as the "active element" or "active electrode" of the probe. When placed into conductive liquid-tissue media and energized, the probe induces electrical current in the conducting liquid and nearby tissue. This current deposits energy into the liquid and tissue, thereby raising the local temperature and creating the desired clinical effect. The highest energy deposition occurs in areas closely proximate to the active tip where current density is largest.

Power density in close proximity to the tip depends primarily on the applied power, the shape and size of the exposed portion of the electrode, the surrounding liquid/tissue electrical conductivity as well as the presence of bubbles. In the sparking regime, the power density also depends on the spark distribution and conductivity (i.e., the plasma conductivity). It is further affected by the size, shape, and position of the return current electrode. In most cases, positioning the return electrode in closer proximity to the active electrode increases the power density in the region near the electrode tip.

In the case of a monopolar probe, the return current is collected by a large return electrode (sometimes called dispersive electrode or return pad) placed on the patient's body, remote from the probe tip. The power concentration capability of a monopolar probe is determined by the shape of the exposed electrode: the smaller and sharper the tip is, the better its power concentration capability.

In the case of bipolar probes, the return current electrode is placed in moderate proximity to the active electrode (generally from 1 to 10 mm). In comparison with a monopolar probe having an active electrode of approximately the same shape, some additional power concentration takes place. The power concentration capability can be further controlled by the shape and position of the return electrode. Decreasing the distance between the return electrode and the active electrode increases the power concentration. A problem arises when the probe is generating sparks. (Recall that this is the goal of probe operation in ablation-tissue evaporation or cutting, for example). If the return electrode is placed sufficiently close to the tip to achieve a substantial increase of power concentration, the breakdown (arcing within bubbles) takes place between the tip and return electrode. The spark conductive channel connects the active electrode to the return current electrode and the power supply is loaded directly by the spark. Usually this leads to an extra high-energy deposition in the spark between metallic electrodes, thereby resulting in localized melting and vaporization of the electrodes themselves. In turn, this results in shorting of the power supply and destruction of both the active and return electrodes with little clinical benefit to the patient.

A good bipolar probe design must therefore avoid arcing between the active and return electrodes. Usually this is achieved by placing the return electrode a sufficiently large distance away from the active electrode to prevent direct breakdown between electrodes. Nevertheless, periodic arcing may take place such that both electrodes are eroded and eventually destroyed, especially in an aggressive mode of operation. Therefore, the additional degree of power concentration achievable by bipolar probes is severely limited.

In contrast, the electrosurgical device of the present invention has one or more additional metallic electrodes which are not connected directly to any part of the power supply circuit, and therefore are called "floating". These floating electrodes are in contact with the tissue and/or liquid in proximity to the active electrode. The electrical potential of these additional electrodes is not fixed, but rather is "floating" and is determined by size and position of the electrode and the electrical conductivity of the tissue and/or liquid surrounding the distal end of the device. This electrode is positioned in such a way that one end of the electrode is in close proximity to the active electrode. Another portion of the floating electrode is positioned in a region of low potential in the liquid and/or tissue. The addition of this floating electrode thereby substantially modifies the electrical field distribution, and energy deposition, in the vicinity of the active electrode without the possibility of electrode destruction since the floating electrode is not directly connected to the electrical power supply.

The floating electrode therefore serves to concentrate the electric field in the region of the active electrode, but it does not provide a current path back to the RF generator that powers the electrosurgical device. In monopolar electrosurgical devices, there is an additional dispersive return electrode that is in contact with a remote portion of the patient's body and is coupled to the RF generator in order to complete the return path. In bipolar electrosurgical devices, there is a return electrode mounted near the active electrode near the distal end of the device, and this return electrode is coupled to the RF generator in order to complete the return path to ground. In either configuration, a floating electrode may be used to shape the electric field near the active electrode; however, the floating electrode should not be confused with the return electrode, as the floating electrode has no connection to the RF generator and is, in fact, isolated from the electrical circuit of the device.

In the absence of sparking (arcing within bubbles), the "floating" electrode increases power density in the vicinity of the probe tip. This is because the floating electrode extends from a high potential region (near the active electrode), to a region with low potential (farther from the active electrode), and "shorts" these points together. The probe's floating will be between the potentials of these points. The presence of the electrode decreases the potential near the active electrode, and thereby increases the electric field, current and power density in the region near the active electrode. A floating electrode works about the same way as any extended conductive object in an electrostatic field. The higher power density results in more efficient liquid heating and steam bubble formation, which, in turn, allows one to decrease the power applied to probe for a given effect. In the presence of the "floating" electrode, more sparks are generated in the active region, since this region is larger. Bubble trapping (the retention of bubbles in selected areas to insulate these areas for improved ablator efficiency) is greatly enhanced with proper design of the floating electrode, insulator and the active electrode.

Sparks are an active element of the electrosurgical process. A spark is generated in a steam bubble if the electrical field in the bubble (voltage difference across a bubble) is sufficient for breakdown. Usually sparks are generated in bubbles that are close to the active electrode of the probe because current density and field intensity are largest in this region.

The breakdown or spark inside a bubble is an electrically conductive channel of partly ionized pressurized gas. This medium is called highly collisional plasma. The basic property of this plasma is that the conductivity is proportional to the plasma density. Higher plasma temperatures are associated with higher ionization rates, plasma densities and conductivity.

Usually energy is deposited into highly collisional plasmas by electric current driven by voltage applied to electrodes at the ends of a plasma channel. In the case of a plasma channel formed inside of a bubble, the inner parts of the bubble surface having the largest voltage difference act as the "electrodes" to which the channel is connected. More frequently, but not always, one of these electrodes is a metallic surface of the active electrode and the other is the opposite surface of the bubble or the surface of the tissue.

Electrically, the plasma channel is characterized by its impedance. The efficiency of energy deposition strongly depends on the ratio between the plasma channel and the power supply impedance. Efficiency (the portion of applied energy deposited to the plasma) as high as 50% can be achieved for matched conditions in which the power supply impedance equals the spark (plasma channel) impedance. If the channel impedance is too large or too small, the power deposition in the plasma is decreased.

As described previously herein, the additional "floating" electrode can significantly increase the energy density in the region surrounding the active electrode. This makes it possible to substantially increase the power deposited into the spark. Since the floating electrode can be placed very close to the probe tip, the largest probability is for breakdown and plasma channel formation in the region between the two electrodes—the active electrode and the floating electrode. The plasma channel current can now be supported not by a bubble size fraction of the induced current, but by a much larger volume of current flow that is determined by the size of floating electrode. This floating electrode additionally concentrates current delivered to the spark. The optimum spark current can be controlled by adjusting the size and position of the floating electrode. Arcing, then, can occur through bubbles between the active and floating electrodes, or from either electrode through bubbles in contact with that electrode.

In summary, the present invention provides an advanced, electrosurgical probe equipped with one or more "floating electrodes" coupled with one or more active electrode uniquely designed and configured for thermal tissue treatment, including tissue ablation and vaporization, preferably in combination with a resectoscope. The floating electrode concentrates the power (i.e., increases the power density) in the active region, which leads to more efficient liquid heating, steam bubble formation, and spark generation in this region. Arcing occurs from the floating electrode as well as the active electrode, thereby resulting in a probe in which the distal tip has a "working" area equal to the "physical" area. This is in contrast to other prior art probes used in electrically conductive liquids which generally have an electrically active area that is significantly smaller than the physical area of the device.

The floating electrode favorably affects bubble formation and trapping, and therefore enhances the probe's performance. This results in high efficiency operation, allowing the surgeon to substantially decrease the applied RF power and thereby reduce the likelihood of patient burns and injury, while at the same time maintaining high performance operation.

The method of the present invention includes the step of positioning the electrosurgical probe adjacent to target tissue at a surgical site so that at least one of the active electrodes and at least a portion of at least one of the floating electrodes are in close proximity to the target tissue. Conductive or non-conductive irrigant may be supplied to the probe distal tip in the region between the active electrode(s) and the target tissue, and between the portion of the floating electrode in close proximity to the tissue, and the target tissue itself. Other portions of the floating electrode(s) may be in contact with target tissue, adjacent tissue, or fluid environment. Vacuum may be supplied via means within the elongated distal portion to the probe distal tip so as to remove excess irrigant as well as ablation products. The probe is energized producing high current density and arcing in portions of the active electrode and floating electrode in close proximity to the target tissue. Lower density current flow from regions of the floating electrode(s) in contact with adjacent target tissue results in desiccation of the adjacent tissue so as to achieve hemostasis. While energized, the probe may be moved across the target tissue with a brushing or sweeping motion, or intermittently energized for a brief period of time and repositioned so as to affect the target tissue. When used with a resectoscope, the probe may be extended axially, energized and retracted proximally so as to cut a groove in the tissue. The process may be repeated until the desired volume of tissue is removed. The movement of the probe relative to the tissue may be manually achieved or alternatively automated, for example, according to the principles outlined in U.S. Pat. No. 6,921,398 or U.S. Patent Publication No. 2003-0065321, the contents of which are incorporated by reference herein in their entirety.

The current invention is also useful for medical procedures in which tissue is thermally treated rather than removed by vaporization, such as, for instance, cardiology, oncology and treatment of tumors, a process sometimes referred to as lesion formation for coagulation and/or denaturing of tissue. In these applications, the device is brought into close proximity, or contact, with tissue with or without the presence of externally applied irrigant at the site for thermal treatment. The voltage applied to the active electrode is reduced to a level which produces current densities insufficient for forming sparks and the associated bubbles. Tissue is heated to a desired temperature for a predetermined time sufficient for lesion formation. The floating electrode intensifies the electric field in the region surrounding the active electrode so as to produce a larger, more controlled and more uniform lesion.

EXAMPLES

Hereinafter, the present invention is described in more detail by reference to the exemplary embodiments. However, the following examples only illustrate aspects of the invention and in no way are intended to limit the scope of the present invention. As such, embodiments similar or equivalent to those described herein can be used in the practice or testing of the present invention.

Referring to FIGS. 1 through 4, which depict an electrosurgical probe specifically configured for use with a resectoscope (not shown) and constructed in accordance with the principles of this invention, probe 100 has an elongated tubular member 102 with a proximal end 104 having an electrical connector 106 suitable for connecting via an electrical cable to an electrosurgical generator, and a distal end 108. Members 110 have proximal ends 112 mounted to distal end 108 of elongated tubular member 102, and distal ends 114 to which are mounted electrode assembly 116. Optional electrode stabilizer 118 for stabilizing the distal end of probe 100 is intended to be proximately disposed to a distal region of a telescope mounted in a resectoscope working element. However, it is envisioned that stabilizer 118 is not required to practice this invention. Conductive member 120 covered by insulation 122 extends from electrical connector 106 to proximal end 124 of insulated conductive member 126.

Referring now to FIGS. 5-8, which depict the distal-most portion of probe 100, referred to herein as the active head, electrode assembly 116 includes active electrode 130, insulator 132 and floating electrode 134. Active electrode 130 has a plurality of grooves 136 of width 138 and depth 140, width 138 and depth 140 being selected to trap bubbles in the grooves. However, as noted previously, the present invention is not limited to the grooved design depicted but encompasses any active electrode ablating surface specifically configured to maximize bubble retention and concentrate power density. So long as the ablating surface performs the desired function (e.g., bubble retention, power density concentration), the specific design, geometry, arrangement and configuration of the array or its components is not particularly limited. Accordingly, the ablating surface may be composed of an array of raised and recessed regions, e.g., a plurality of walls and grooves, a plurality of elevated pins, a plurality of bumps and pockets, or a combination thereof. As noted previously, the array be continuous or discontinuous, evenly or unevenly spaced, composed of raises and recesses that are linear or non-linear (e.g., curvilinear, wavy, zigzagged, angled, etc.), parallel or circumferential positioned, or the like.

Figure 8:
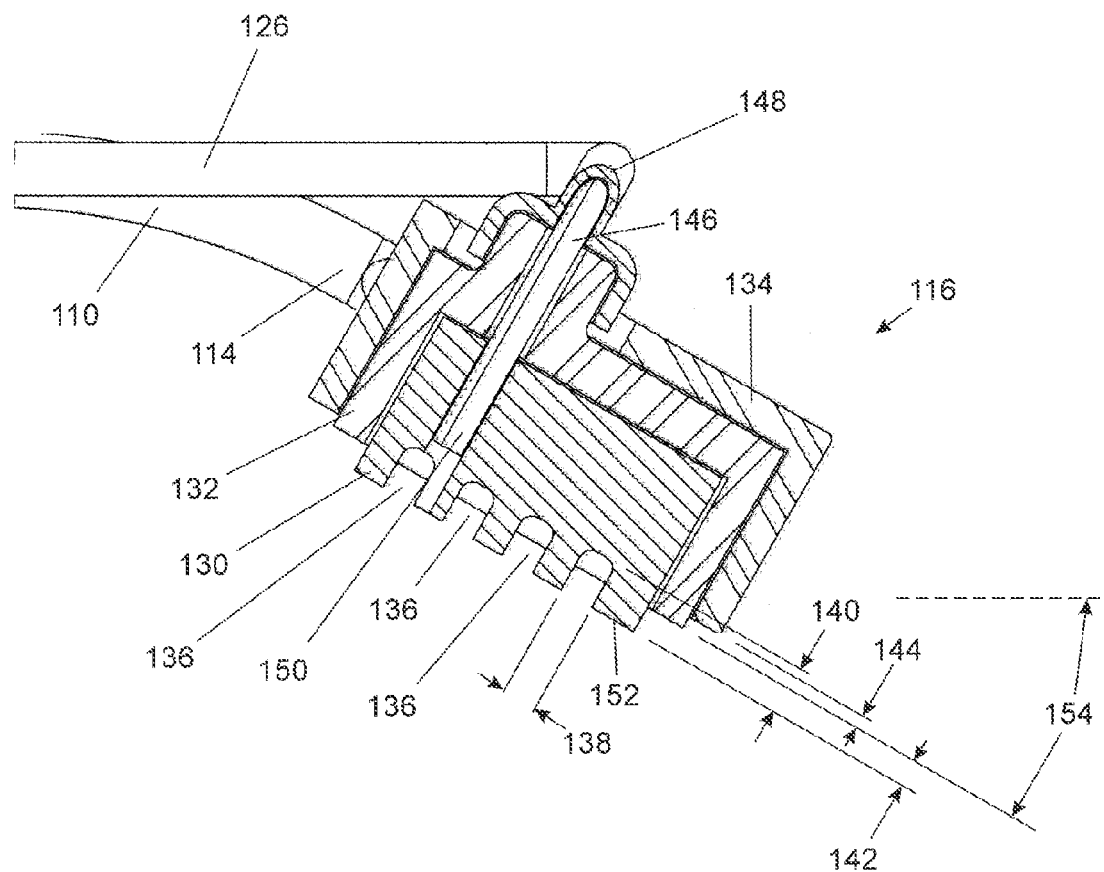
FIG. 8 is a side elevational sectional view of the objects of FIG. 5.

Active electrode 130 and floating electrode 134 are preferably formed from a suitable metallic material, examples of which include, but are not limited to, stainless steel, nickel, titanium, tungsten, and the like. Insulator 132 is preferably formed from a suitable dielectric material, example of which include, but are not limited to, alumina, zirconia, and high-temperature polymers. As shown in FIG. 8, active electrode 130 preferably protrudes beyond insulator 132 a distance 142. In turn, insulator 132 preferably protrudes beyond floating electrode 134 a distance 144. Insulated conductive member 126 has a conductive portion 146 coated with dielectric material 148. Distal end 150 portion 146 is connected to active electrode 130. Active electrode 130 has surface 152 segmented by grooves 136. Surface 136 forms an acute angle 154 with the axis of tubular member 102. Angle 154 is preferably between 0 and 90 degrees, more preferably between 5 and 80 degrees, more preferably between 10 and 70 degrees, more preferably between 15 and 60 degrees, even more preferably between 20 and 50 degrees.

Figure 9:
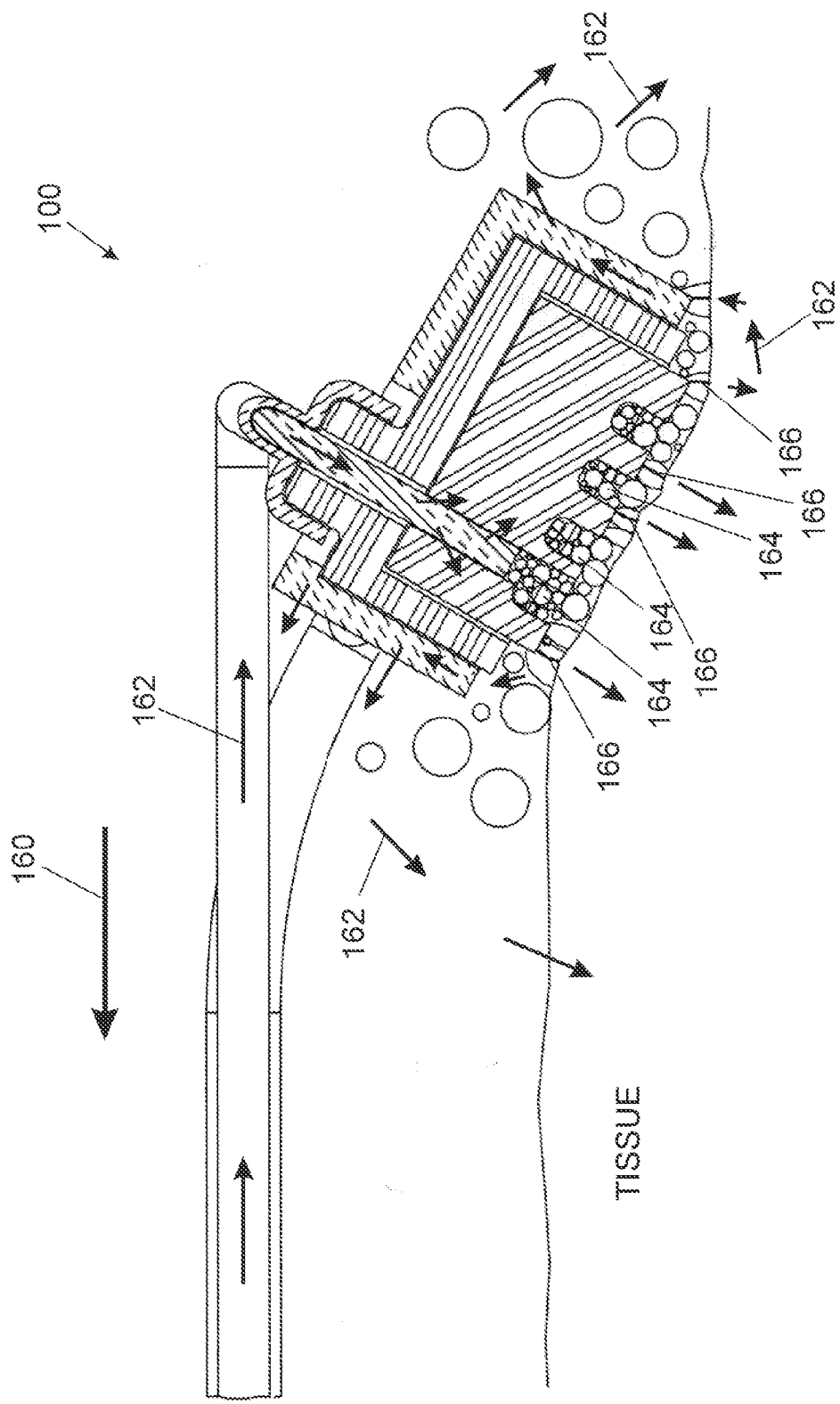
FIG. 9 is a side elevational sectional view of the objects of FIG. 5 during use.

Referring now to FIG. 9, which depicts a probe 100 in use in a conductive liquid environment, probe 100 is moved axially in direction 160 relative to the tissue which is connected to a return electrode at a remote location. Current (depicted by arrows 162) flows from conductor 126 to active electrode 130, and then from active electrode 130 through the conductive fluid to the tissue and the return electrode. A portion of the current flows through the floating electrode, the current entering the portion of the floating electrode in the high-potential portion of the electric field in close proximity to the active electrode, and exiting in portions of the floating electrode in low-potential regions farther removed from the active electrode. Current flowing through the conductive liquid heats the liquid, the heating at a location being proportional to the current density at that location. Where the current density is sufficient, the conductive liquid boils, forming steam bubbles. Some of the bubbles 164 are trapped in grooves 136 where their presence decreases current flow from the surfaces of the groove, thereby effectively insulating the groove. Other bubbles form at surface 152. When these bubbles reach a sufficient size, arcing 166 occurs within some of these bubbles, the resistance to arcing being less than the resistance of the alternate path for current flow around the bubble. In some cases, the bubbles at surface 152 intersect portions of tissue that are in close proximity. When arcing occurs within these bubbles, the arc is between active electrode 130 and the tissue, and in this manner a portion of the tissue is vaporized. Current density at the portions of the floating electrode in high-potential portion of the electric field, in close proximity to the active electrode, also may be sufficient to cause boiling of the liquid, bubble formation, arcing within bubbles, and arcing between the floating electrode and tissue so as to vaporize tissue.

Figure 10:
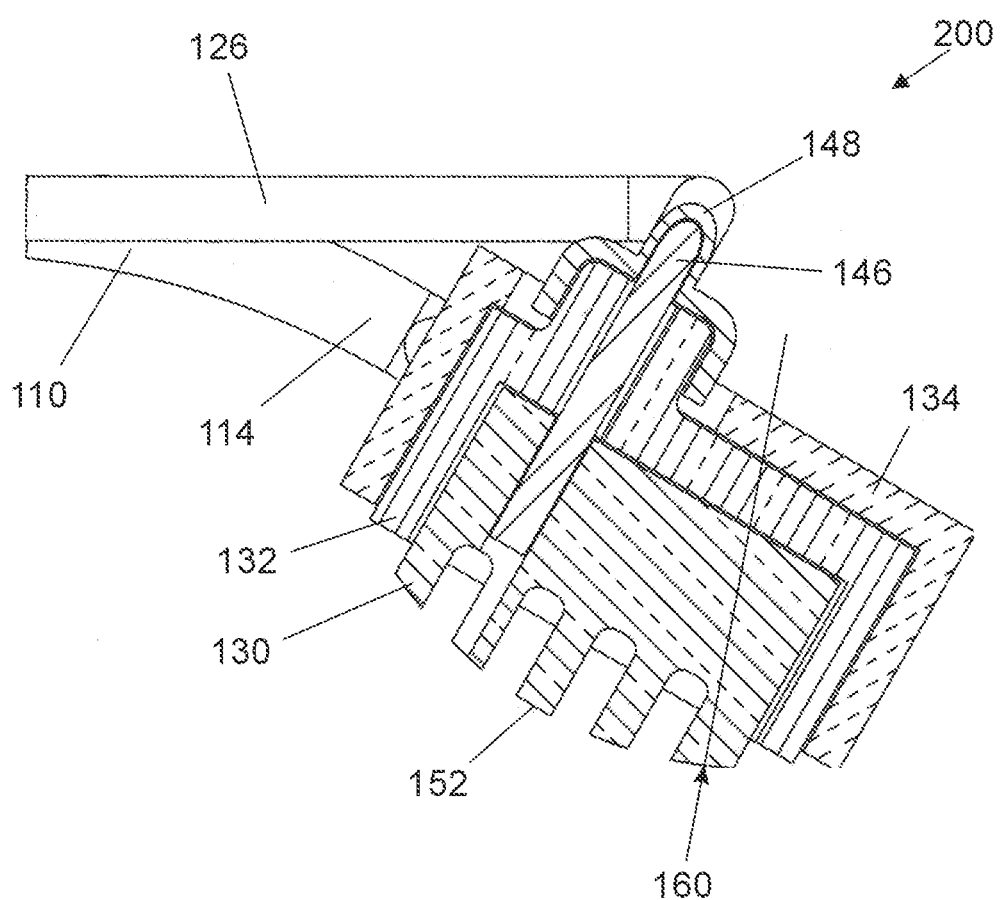
FIG. 10 is a side elevational sectional view of the distal-most portion of an alternate embodiment.
Figure 11:
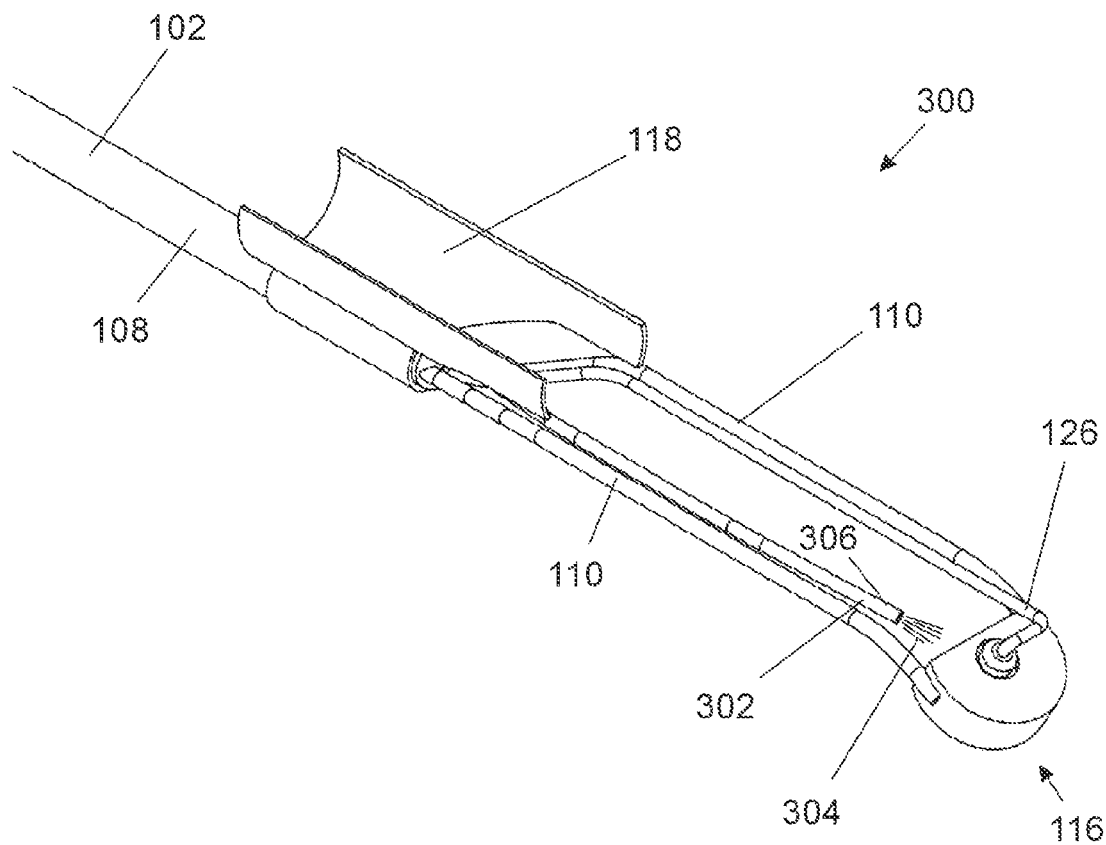
FIG. 11 is a perspective view of another alternate embodiment.
Figure 12:
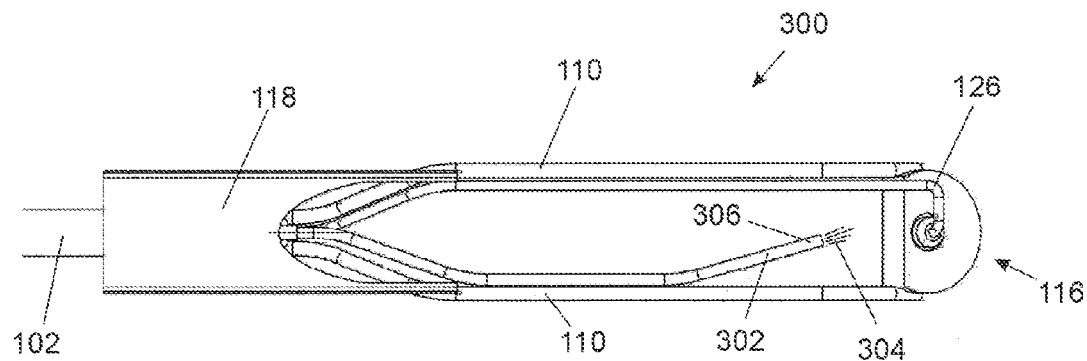
FIG. 12 is a plan view of the objects of FIG. 11.
Figure 13:
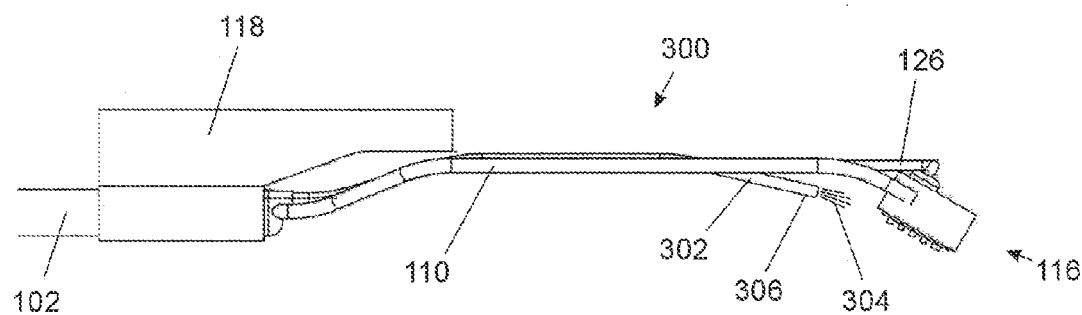
FIG. 13 is a side elevational view of the objects of FIG. 11.
Figure 14:
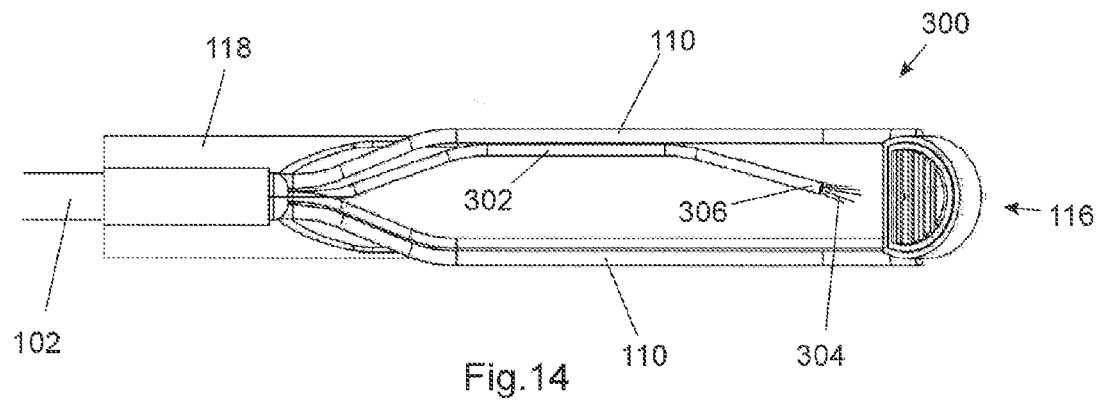
FIG. 14 is a bottom side plan view of the objects of FIG. 11.
Figure 15:
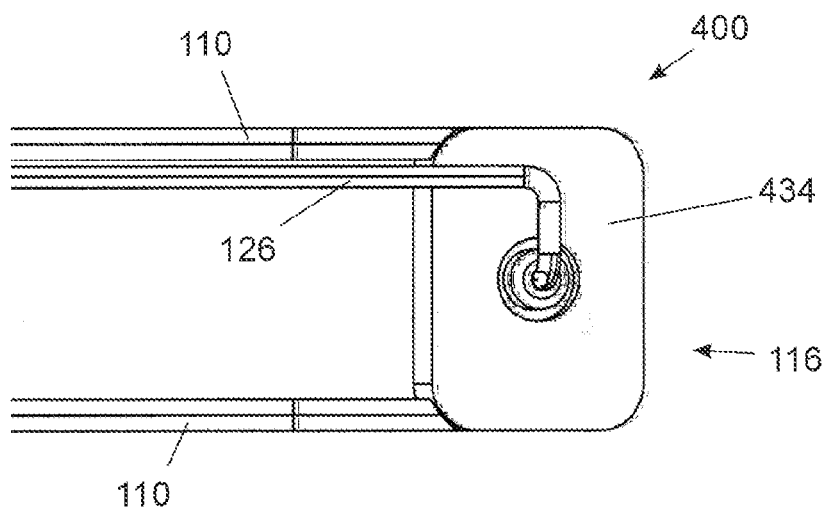
FIG. 15 is a plan view of an alternate embodiment.
Figure 16:
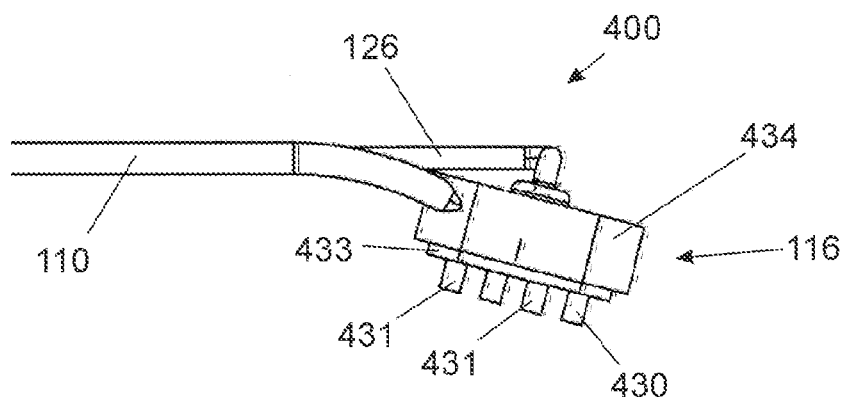
FIG. 16 is a side elevational view of the objects of FIG. 15.
Figure 17:
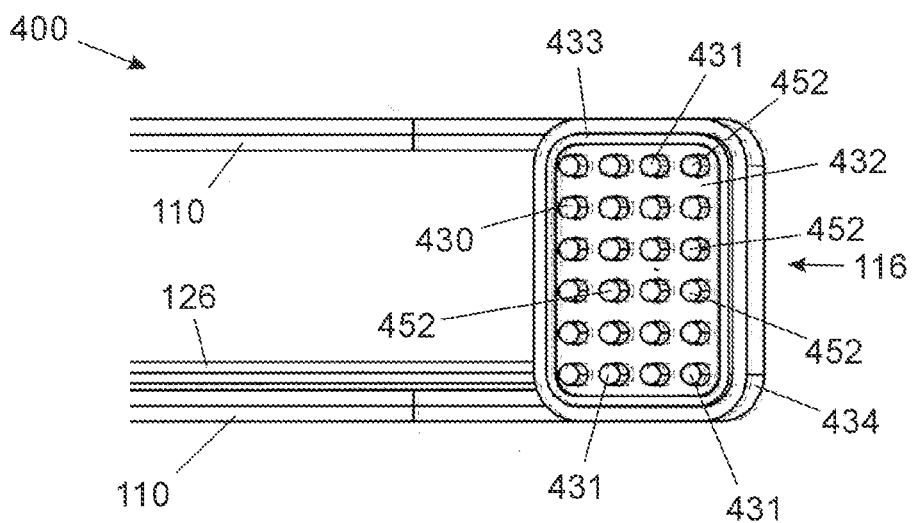
FIG. 17 is a bottom side plan view of the objects of FIG. 15.
Figure 18:
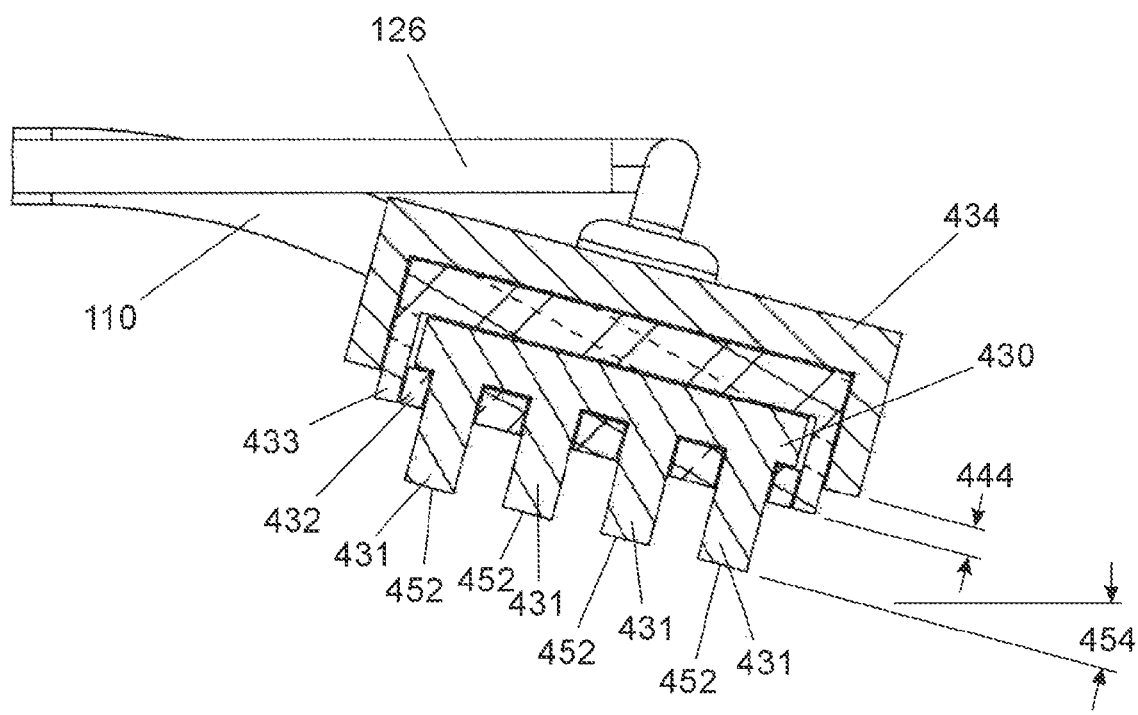
FIG. 18 is an expanded side elevational sectional view of the distal-most portion of the objects of FIG. 15.

The active or ablating surface 152 of active electrode 130 of probe 100 is preferably planar. However, in some circumstances, it may be advantageous to have surface 152 be other, non-planar forms. For example, in an alternate embodiment shown in FIG. 10, active surface 152 of probe 200 is curved, preferably in a cylindrical manner having a radius 160. In other embodiments, surface 152 may have other curvilinear profiles. In still other embodiments, surface 152 may have a non-uniform cross-section and take the shape of, for example, a convex spherical segment or a concave spherical segment.

Probe 100 is intended for use at a surgical site which is submerged in liquid environment or in which the region surrounding the distal end of the probe is irrigated with a irrigant. Probe 300, shown in FIGS. 11 through 14, is identical in construction to probe 100, and additionally has a means for providing irrigant to a surgical site, particularly the region surrounding the distal portion of the probe. Tubular member 302 is connected via means within tubular member 102 to an external irrigant source. Flow 304 from distal end 306 of member 302 causes puddling of irrigant in the region surrounding electrode assembly 116 and tissue in contact with it.

FIGS. 15 through 18 depict an alternate embodiment, including an active electrode configured for thermal treatment or vaporization of tissue in a fluid environment. Probe 400, the distal portion of which is depicted in FIGS. 15 through 18, is constructed a fashion analogous to that of probe 100, with the exception of electrode assembly 116. Active electrode 430 forms an array of cylindrical pins 431 which protrude through holes in insulator portion 432, which with insulator portion 433 electrically isolate active electrode 430. Insulator portion 432 protrudes from floating electrode 434 distance 444. Axial surfaces 452 of pins 431 are coplanar and form an acute angle 454 with the axis of tubular portion 102 (FIG. 1). In this context, the acute angle may range between 0 and 90 degrees, more preferably between 5 and 80 degrees, more preferably between 10 and 70 degrees, more preferably between 15 and 60 degrees, even more preferably between 20 and 50 degrees.

Figure 19:
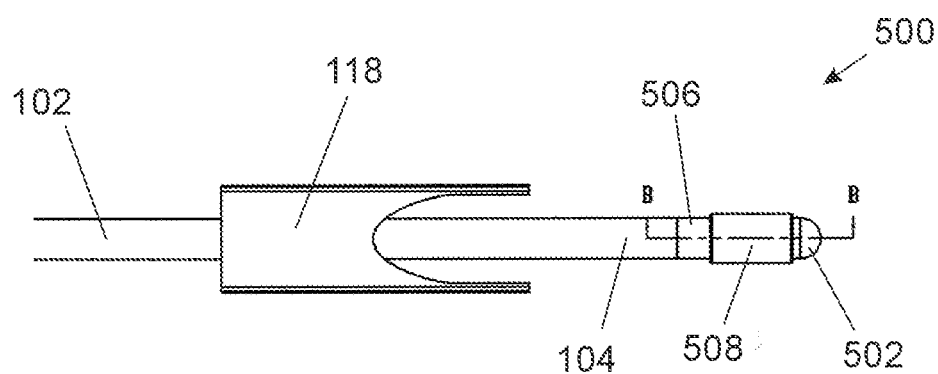
FIG. 19 is a plan view of another alternate embodiment.
Figure 20:
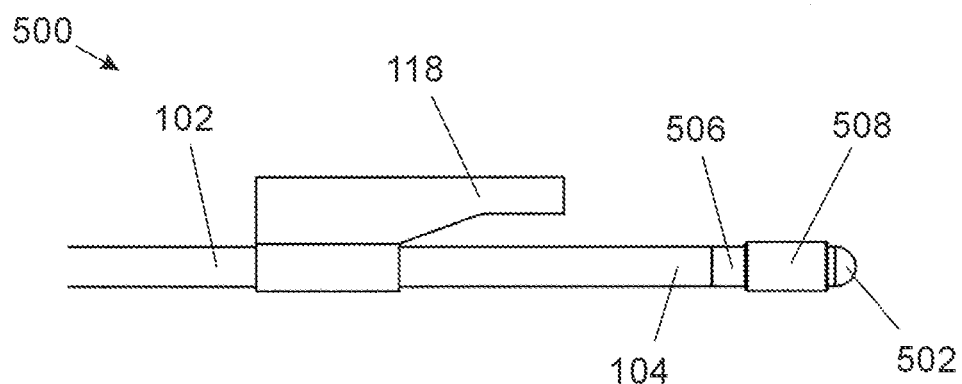
FIG. 20 is a side elevational view of the objects of FIG. 19.
Figure 21:
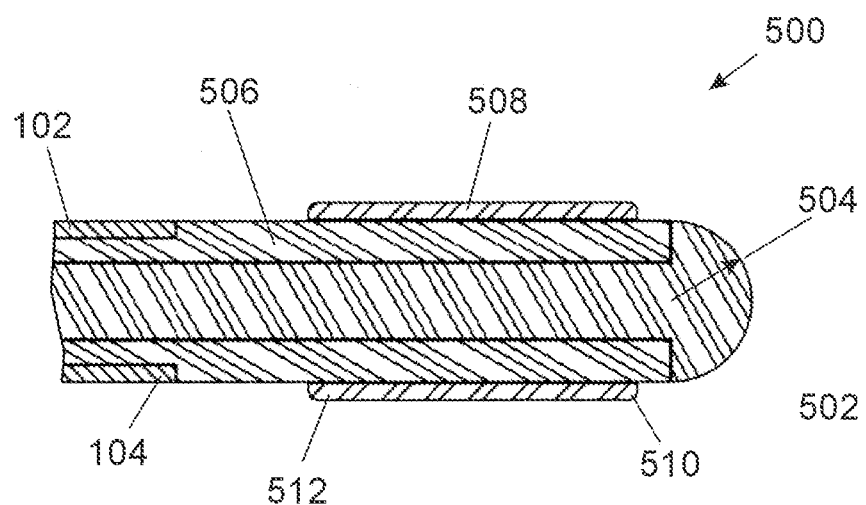
FIG. 21 is an expanded side elevational sectional view of the distal-most portion of the objects of FIG. 19.

It is frequently desirable to precisely vaporize or thermally treat small regions of tissue. The embodiment shown in FIGS. 19 through 21 has an active electrode that forms a hemispherical portion of radius 504. Probe 500 is analogous in construction to probe 100, including an elongated tubular portion 102 with a proximal end electrical connector 106 connected by means within portion 102 to the active electrode, and a scope support 118. Active electrode 502 forms a hemisphere of radius 504. Insulator 506 is mounted to distal end 104 of tubular portion 102. Tubular floating electrode 508 is mounted to insulator 506. When energized in a conductive fluid environment, floating electrode 508 intensifies the field in close proximity to active electrode 502. Distal end 510 of floating electrode 508 is in a high potential region of the field. Proximal end 512 of floating electrode 508 is in a lower potential portion of the field such that current flows through floating electrode 508 from distal end 510 to lower potential portions. This current flow increases the field intensity thereby increasing the efficiency of the probe. This, in turn, allows procedures to be performed with less power or more quickly.

Figure 22:
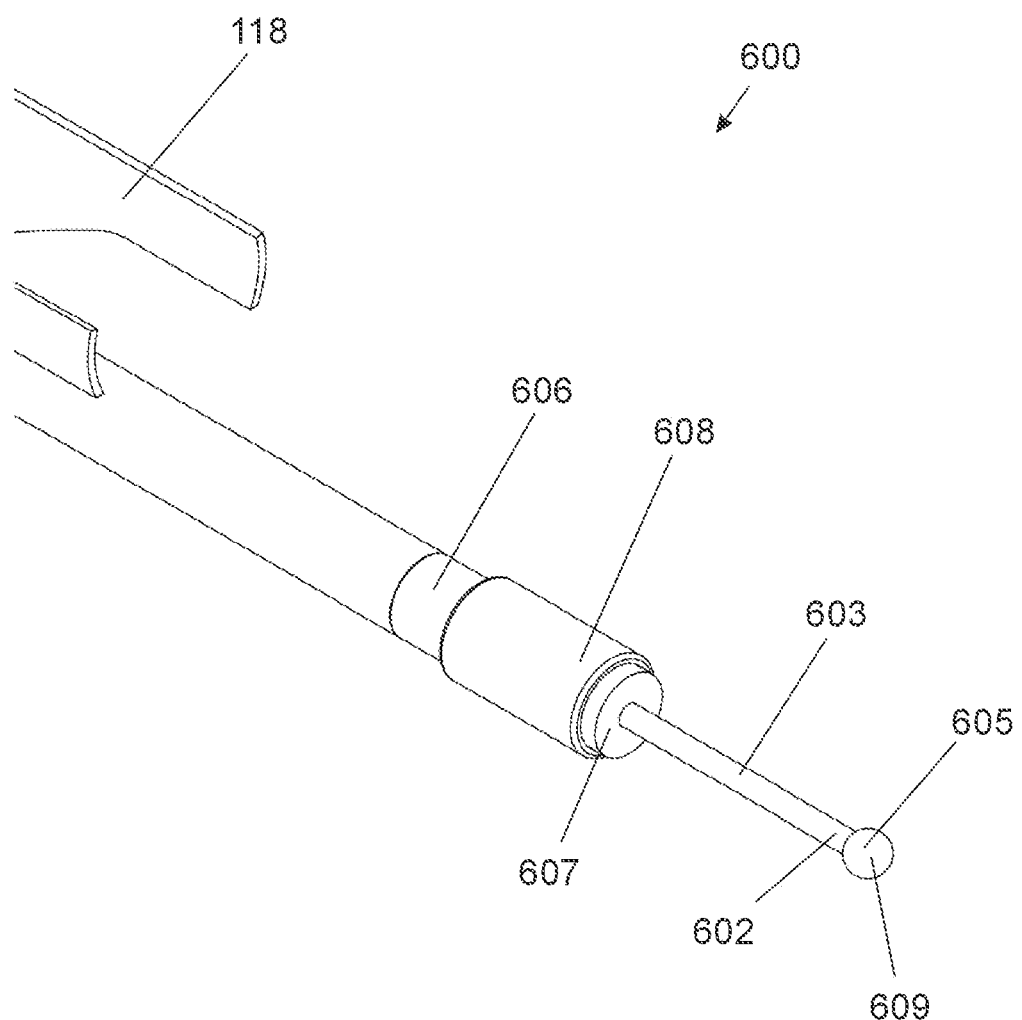
FIG. 22 is a perspective view of another alternate embodiment.
Figure 23:
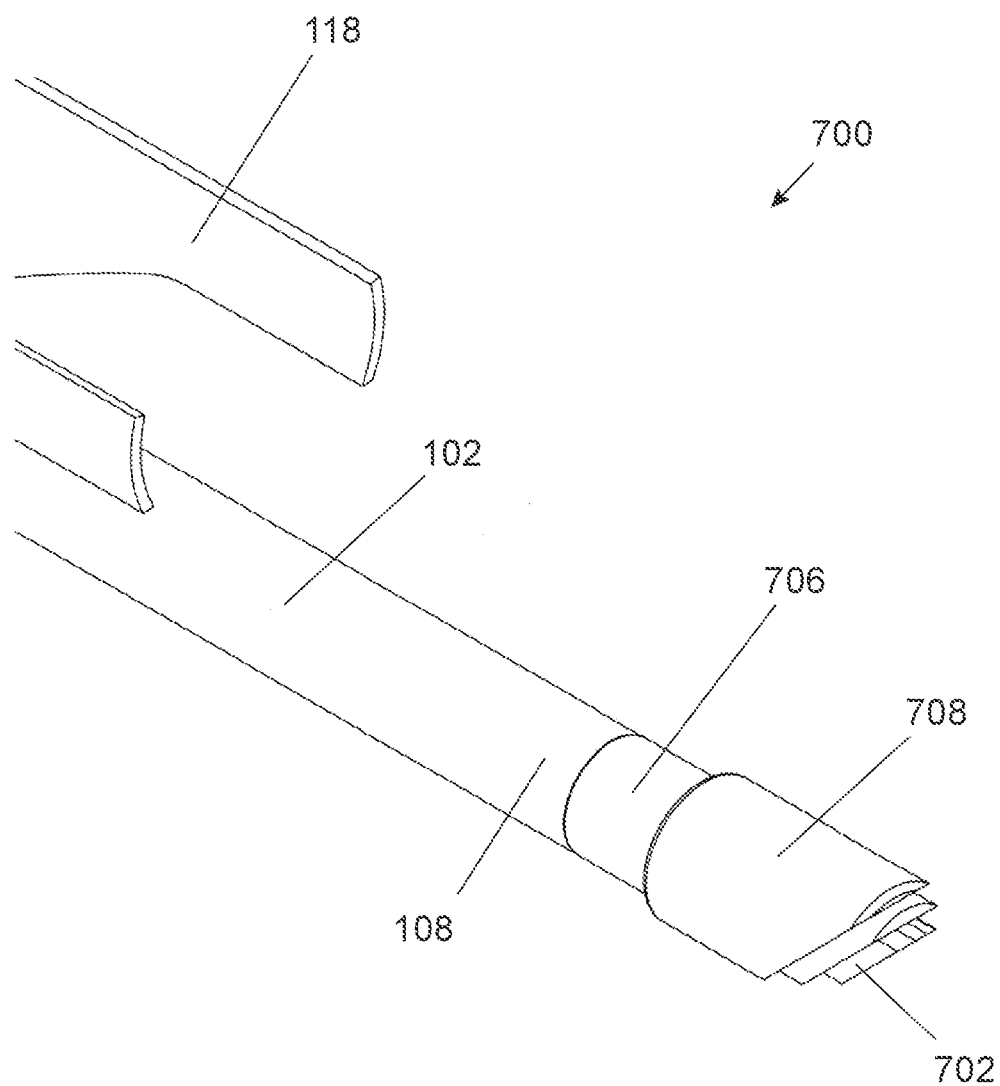
FIG. 23 is a perspective view of yet another alternate embodiment.
Figure 24:
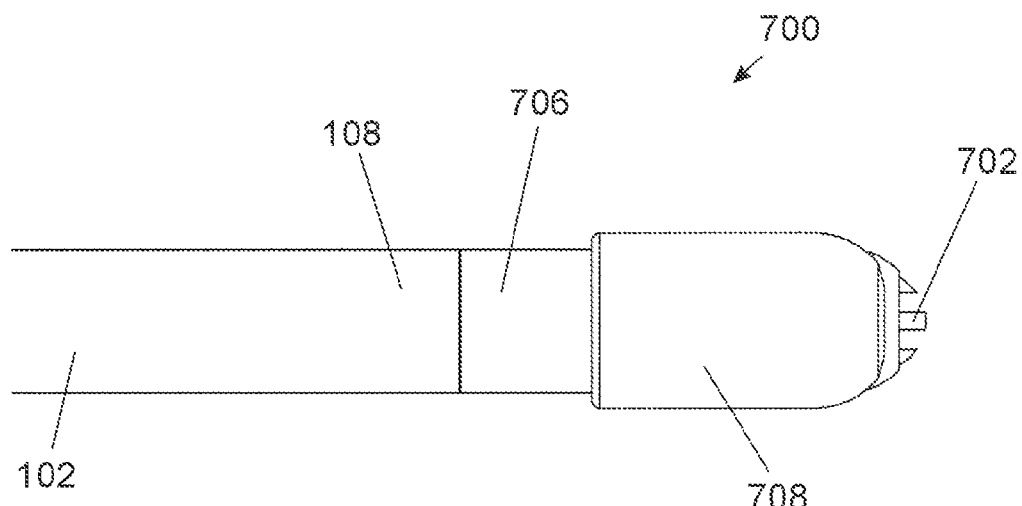
FIG. 24 is a expanded plan view of the distalmost portion of the objects of FIG. 23.
Figure 25:
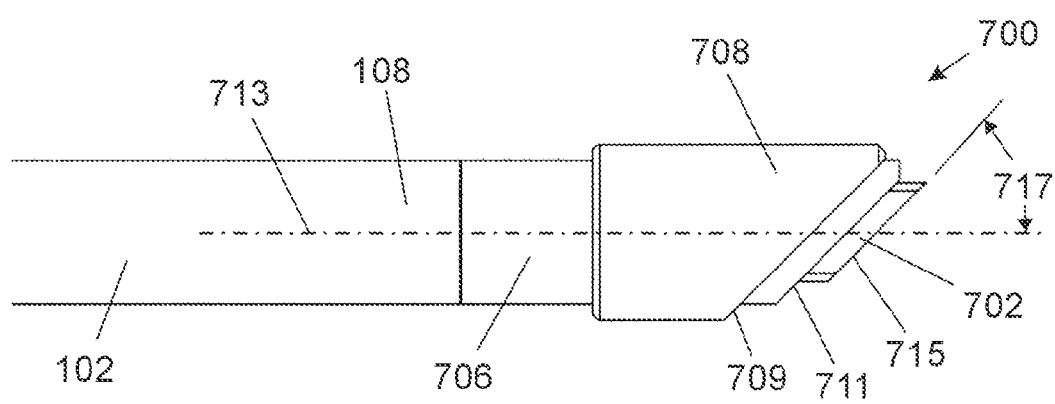
FIG. 25 is a side elevational view of the objects of FIG. 24.
Figure 26:
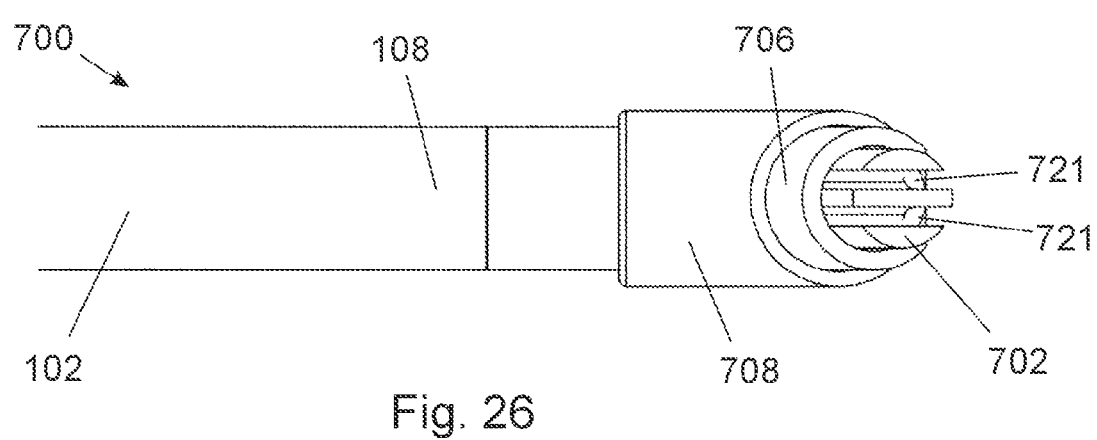
FIG. 26 is a bottom side plan view of the objects of FIG. 24.
Figure 27:
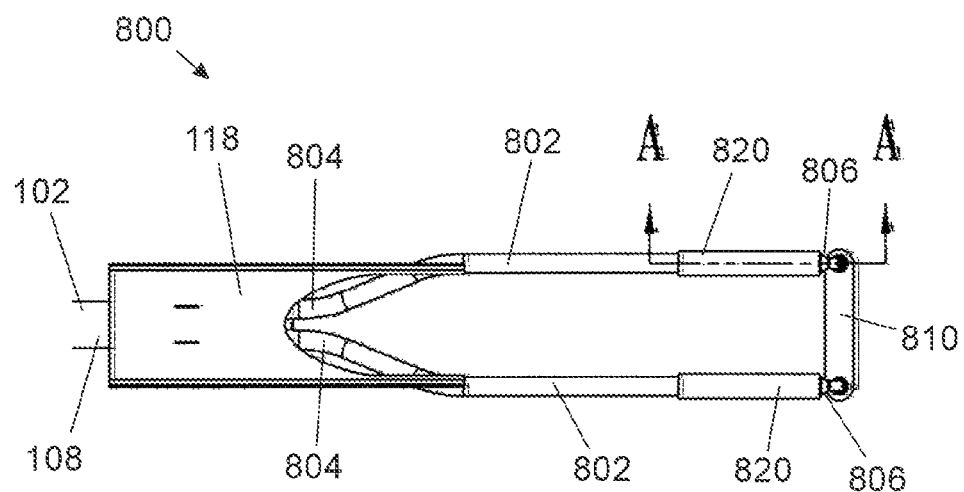
FIG. 27 is a plan view of the distal portion of an alternate embodiment.
Figure 28:
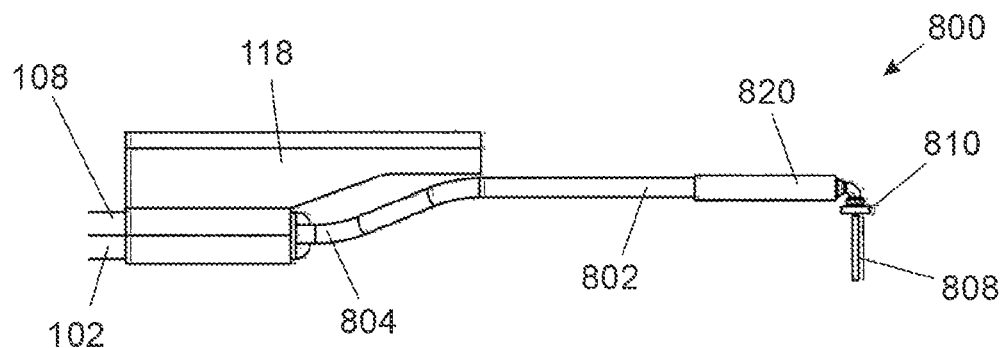
FIG. 28 is a side elevational view of the objects of FIG. 27.
Figure 29:
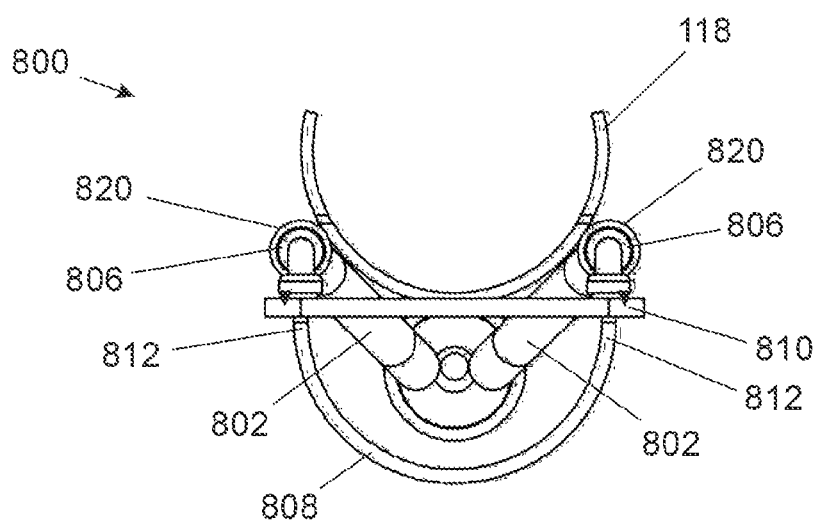
FIG. 29 is an expanded distal end view of the objects of FIG. 27.
Figure 30:
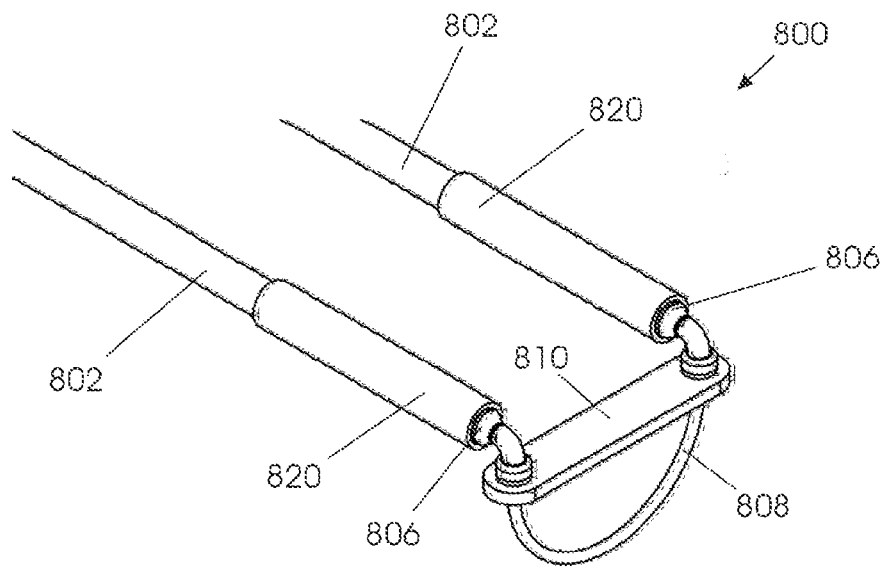
FIG. 30 is a perspective view of the objects of FIG. 27

A further embodiment, intended for cutting, vaporizing or thermally treating tissue, is depicted in FIG. 22. Probe 600 is constructed like probe 500 except that active electrode 602 forms an elongated portion 603 protruding from distal surface 607 of insulator 606. Elongated portion 603 has a distal end 605 forming a spherical portion 609. In other embodiments, portion 603 may be cylindrical throughout its entire length. In still other embodiments, distal end 605 forms a conical point. Floating electrode 608 functions in the same manner as with probe 500. That is, floating electrode 608 intensifies the electric field so as to increase the efficiency of probe 600 when vaporizing or thermally treating tissue.

Another embodiment, the distal portion of which is depicted in FIGS. 23 through 26, uses bubble trapping and a floating electrode to aggressively vaporize tissue. Probe 700 is analogous in construction to probes 500 and 600, comprised of an insulator 706 mounted to distal end 108 of tubular portion 102, a tubular floating electrode 708 mounted to insulator 706, and an active electrode 702 protruding from the distal portion of insulator 706. Active electrode 702 has a distal-most surface 715 inclined at angle 717 to axis 713. Angle 717 preferably ranges between 0 and 90 degrees, more preferably ranges between 5 and 60 degrees, more preferably between 10 and 55 degrees, even more preferably between 30 and 50. Distal-most surfaces 709 of floating electrode 708 and 711 of insulator 706 are approximately parallel to distal-most surface 715 of active electrode 702. Grooves 721 are of a depth and width suitable for trapping bubbles as taught in the description of probe 100.

Cutting loop electrodes are well known in the art. For example, Grossi et al, in U.S. Pat. No. 4,917,082, describes a resectoscope electrode that utilizes a formed wire cutting loop as the active electrode. The electrode, intended for use in non-conductive liquids, has insulating tubes (elements 51 and 53 of Grossi FIG. 2) which cover inner sleeves (elements 50 and 52 of Grossi FIG. 2) but cover no portion of the cutting loop (element 48 of Grossi FIG. 2). This is typical of probes designed for use with non-conductive irrigants since, if the irrigant is ideally non-conductive, current flows only from those portions of the uninsulated portions which are in contact with or sufficiently close proximity to tissue. If such a probe is placed in a conductive fluid environment, current flows from all uninsulated surfaces, both those of the formed wire electrode and uninsulated portions of the conductive members. A large portion of the power applied to the probe would flow into the fluid so as to heat the fluid with no clinical benefit. This power loss would necessitate the use of high power levels to achieve the desired cutting action.

Figure 31:
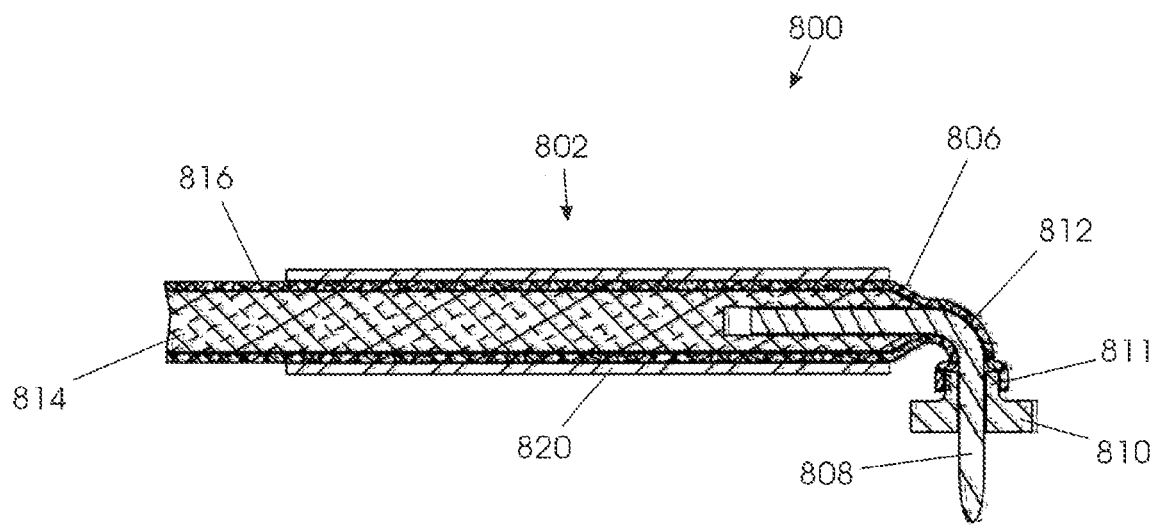
FIG. 31 is a side elevational sectional view of the objects of FIG. 27 at location A-A of FIG. 27.

FIGS. 27 through 31 depict a cutting loop electrode configured for use in a liquid environment and constructed in accordance with the principles of this invention. Probe 800, the distal portions of which are shown in the figures, has a pair of laterally opposed, distally extending, insulated conductive members 802 having proximal ends 804 assembled to distal end 108 of tubular member 102. Conductive members 802 are connected via conductive member 120 to proximal end connector 106 (FIG. 1). Distal ends 806 of members 802 have mounted thereto formed electrode 808. Bubble trap 810, made from a suitable dielectric material, is mounted to upper portions 812 of electrode 808. As best seen in FIG. 31, members 802 have a conductive inner portion 814, an insulating coating 816 which covers distal ends 806, upper portion 812 of electrode 808, and portion 811 of bubble trap 810. Tubular floating electrodes 820 are mounted to members 802 adjacent to distal ends 806 of members 802.

Figure 32:
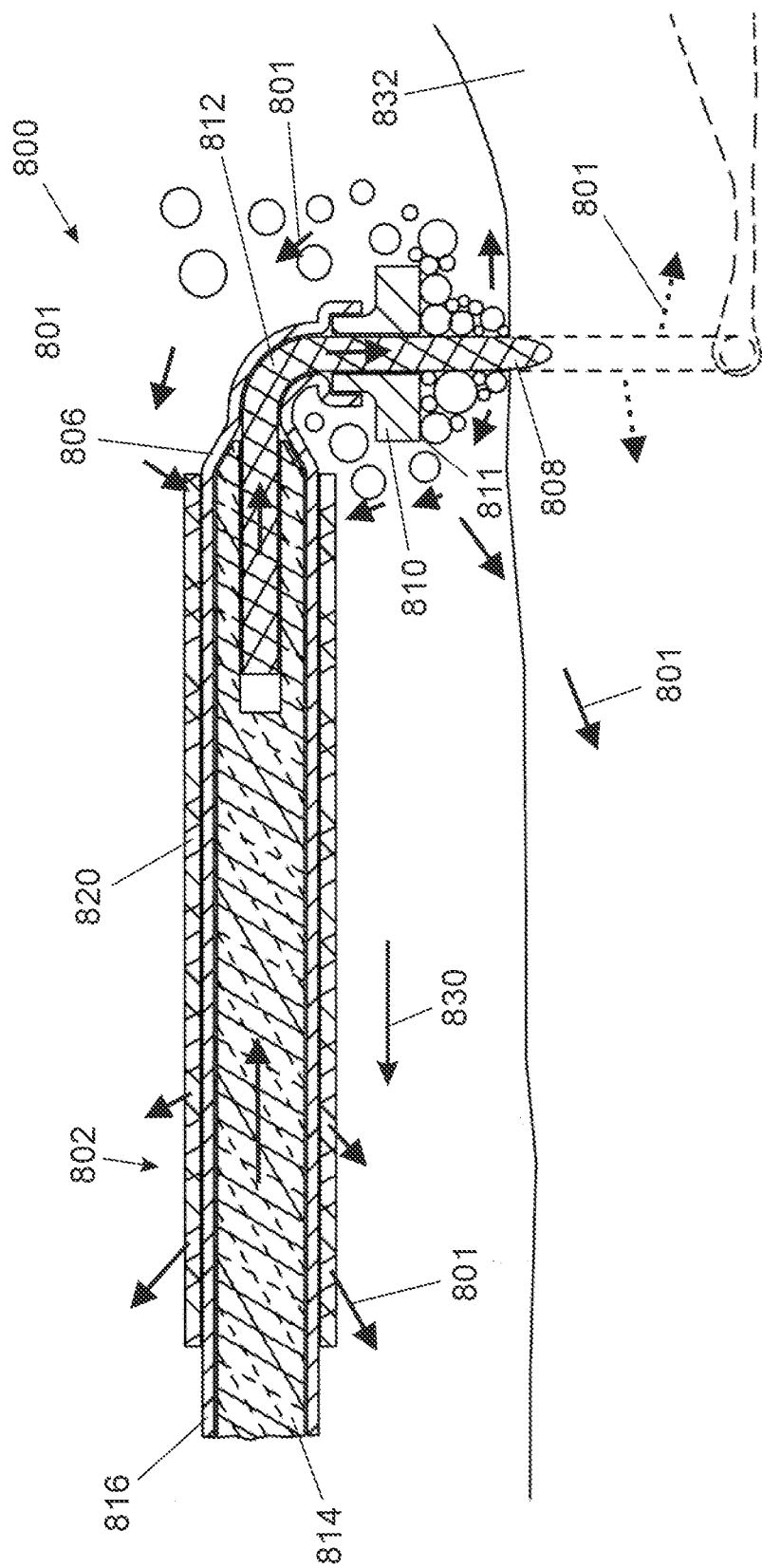
FIG. 32 is a side elevational sectional view of the objects of FIG. 27 in use.

Referring now to FIG. 32 which depicts loop electrode 800 in use, electrode 800 is moved in a proximal direction 830 relative to tissue at the surgical site such that electrode 808 removes a portion of tissue 832. Where electrode 808 is in contact with tissue, current 801 flows from active electrode 808 into the tissue, the high current density present causing vaporization of tissue so as to allow portion 832 to be separated from the remaining tissue. Current also flows from portions of electrode 808 which are uninsulated and in contact with the liquid environment, the current density being sufficient to cause boiling of the fluid adjacent to the wire, and arcing within some of the bubbles. The arcing begins when a bubble reaches a critical size, and stops when the bubble reaches a size which will no longer support arcing. Bubbles which are too large to support arcing may remain in contact with the active electrode due to surface tension, such bubbles thereby insulating the portion of the electrode surface to which they adhere. The buoyancy of the bubbles, and natural convection currents resulting from the heating of the water, act on the bubbles causing them to dislodge from the electrode surface. Conductive flow along the surface of electrode 808 must flow around bubble trap 810, the deflection of the flow causing a region to form beneath bottom surface of bubble trap 810 which is shielded from the convective flow. Bubbles are retained against surface by surface tension, and by the buoyancy of the bubbles. Bubbles beneath these bubbles tend to remain in the region because of surface tension, shielding from convection currents, and buoyancy of the bubbles. The presence of the bubbles, particularly large bubbles, partially insulates the portions of electrode 808 above the tissue so as to reduce current flow from these portions thereby increasing the efficiency of probe 800.

During use, current (represented by arrows 801) flows from 808 active electrode to the tissue or to the liquid environment. A portion of the current flows through floating electrode 820, entering distal portion which is in a high-potential portion of the electric field formed by active electrode 808, and leaving from floating electrode 820 in more proximal portions which are in lower potential portions of the electric field. The current then flows to the return which may be a dispersive pad, or a return electrode located on the instrument. As with other embodiments, the current flow through the floating electrodes increases the current density in the portions of the field around the floating electrodes. This increased current density increases current flow at the active electrode thereby increasing the electrode efficiency.

Figure 33:
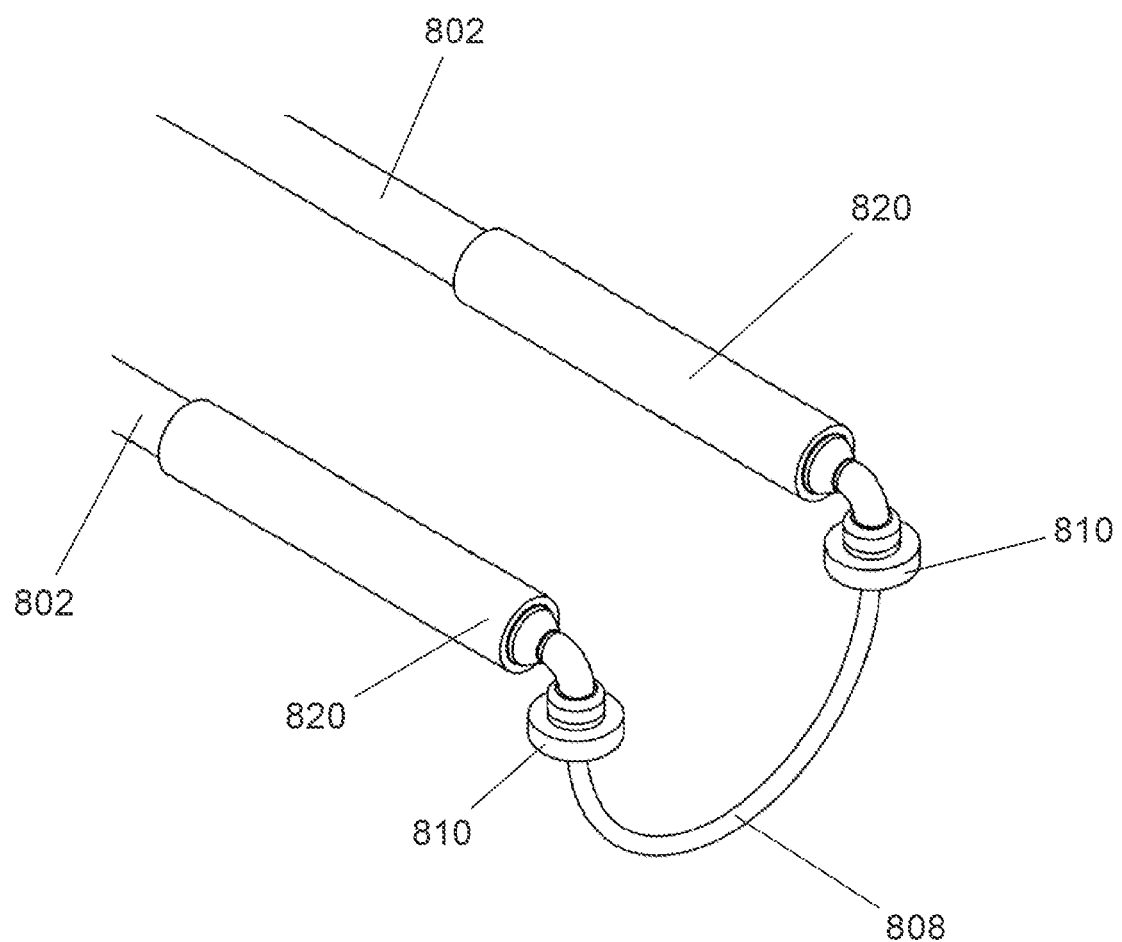
FIG. 33 is a perspective view of the distal portion of an alternate embodiment.
Figure 34:
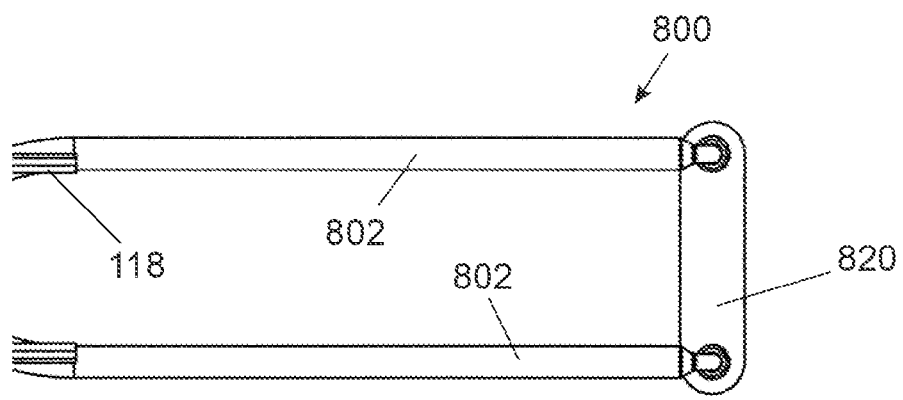
FIG. 34 is a plan view of the distal portion of an alternate embodiment.
Figure 35:
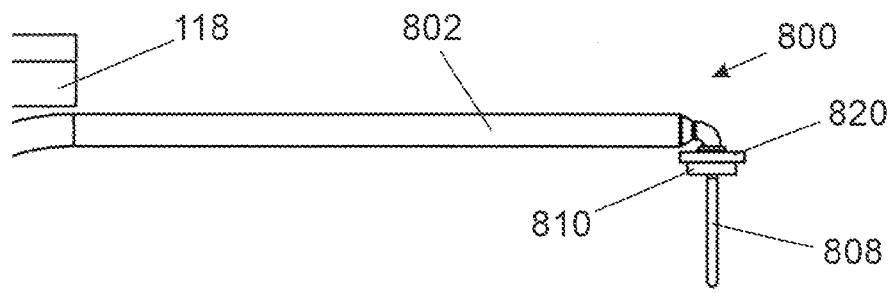
FIG. 35 is a side elevational view of the objects of FIG. 34.
Figure 36:
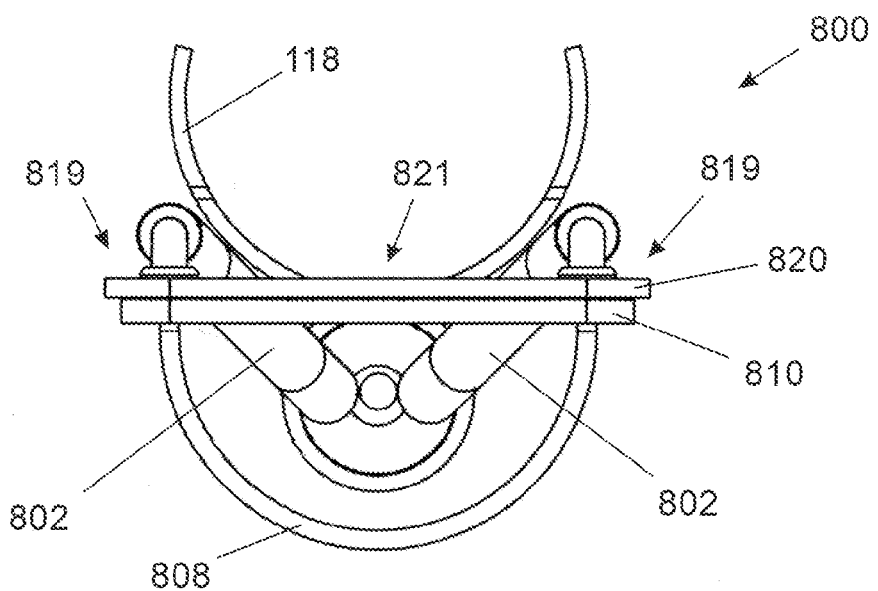
FIG. 36 is an expanded distal end view of the objects of FIG. 34.

Other configurations of the bubble trap and floating electrode are contemplated in the present invention. For instance, FIG. 33 shows an alternate embodiment in which bubble traps 810 are circular members attached to upper portions 812 (see FIG. 31) of electrode 808. Bubble traps 810 function in the same manner as those of the embodiment depicted in FIGS. 27 through 32. In other embodiments, bubble traps 810 have other shapes such as, for instance, elliptical, oblong, or an irregular shape when viewed in plan view as in FIG. 27. In other embodiments, surface 811 may be non-planar, for example concave, or with raised edges so as to better retain bubbles in contact with surface 811. FIGS. 34 through 36 depict an alternate embodiment in which floating electrode 820 is a planar plate mounted to the upper surface of bubble trap 810. Lateral portions 819 of floating electrode 820 in close proximity to active electrode 808 are in high-potential regions of the electric field. Medial portion 821 of floating electrode 820 is in a lower potential region of the electric field. Current flow in the floating electrode is from the high-potential regions in close proximity to active electrode 808 to medial regions in lower potential regions. This current flow, as with previous embodiments, increases current density in region of the active electrode thereby increasing the instrument efficiency.

Figure 37:
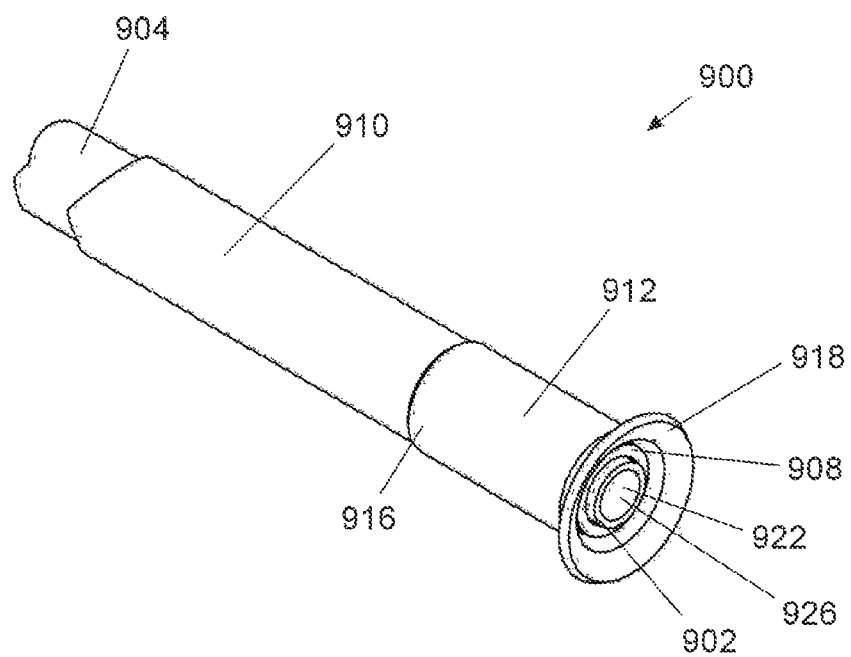
FIG. 37 is a perspective view of the distal portion of an alternate embodiment for ablating kidney stones.
Figure 38:
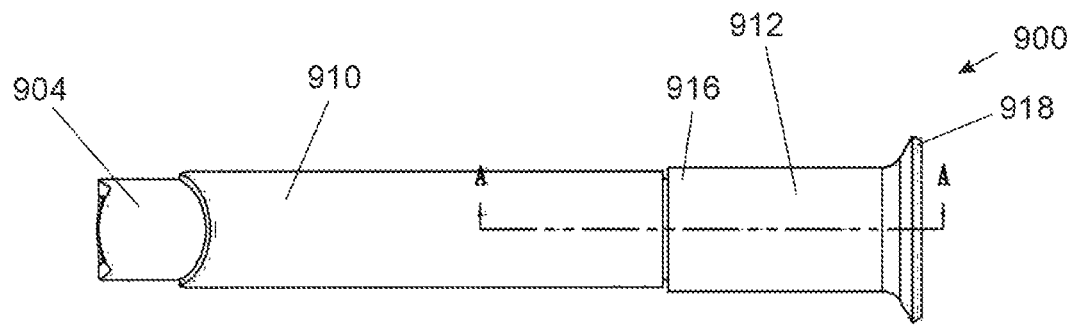
FIG. 38 is a plan view of the objects of FIG. 37.
Figure 39:
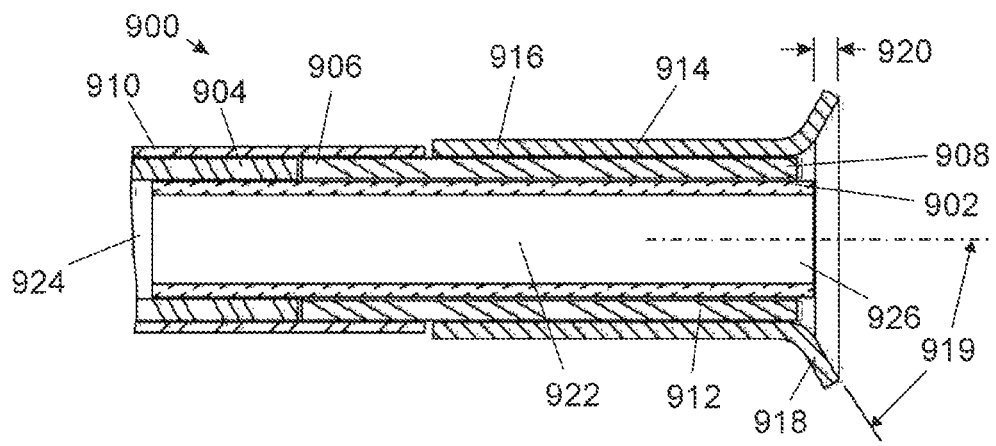
FIG. 39 is an expanded side elevational sectional view of the objects of FIG. 37 at location A-A of FIG. 38.

Yet another disclosed embodiment may be used to reduce the size of kidney stones so that they can be aspirated from the patient. Referring to FIGS. 37 through 39 which depict the distal portion of an ablator probe for eroding kidney stones, probe 900 has a tubular active electrode 902 which is assembled to tubular member 904 such that active electrode 902 is electrically connected to proximal electrical connector 106 (FIG. 1). Tubular member 904 and proximal end 906 of ceramic insulator 908 are covered by dielectric coating 910. Floating electrode 912 is mounted to distal portion 914 of insulator 908. Floating electrode 912 has a cylindrical proximal portion 916, and a flared distal portion 918 protruding beyond active electrode 902 by a distance 920. Lumen 922 of active electrode 902 and lumen 924 of tubular member 904 together form an aspiration path between the distal opening 926 of active electrode 902 and an external vacuum source. In a preferred embodiment, the external vacuum source has a means for controlling the vacuum level.

Figure 40:
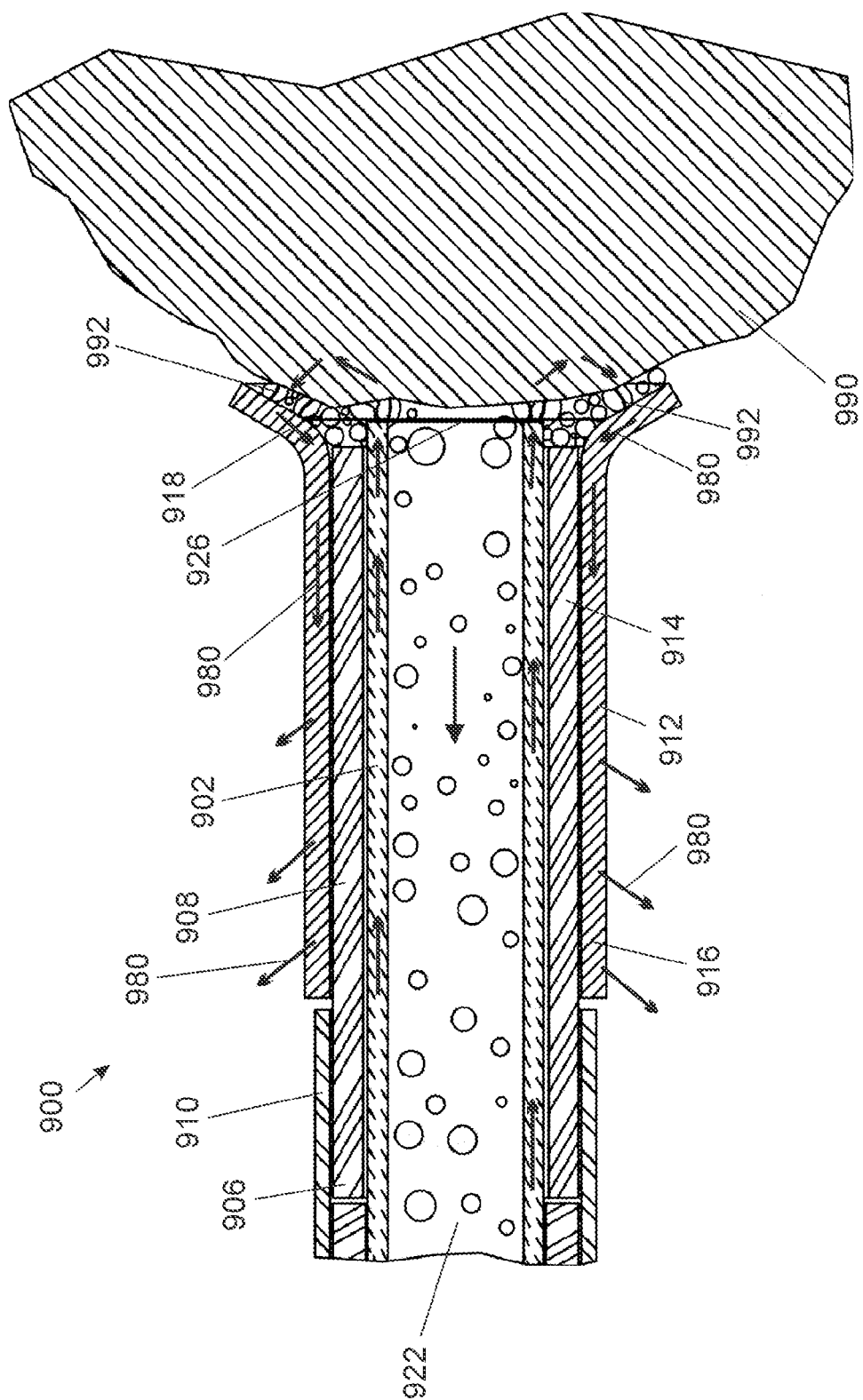
FIG. 40 is an expanded side elevational sectional view of the objects of FIG. 37 during use.
Figure 43:
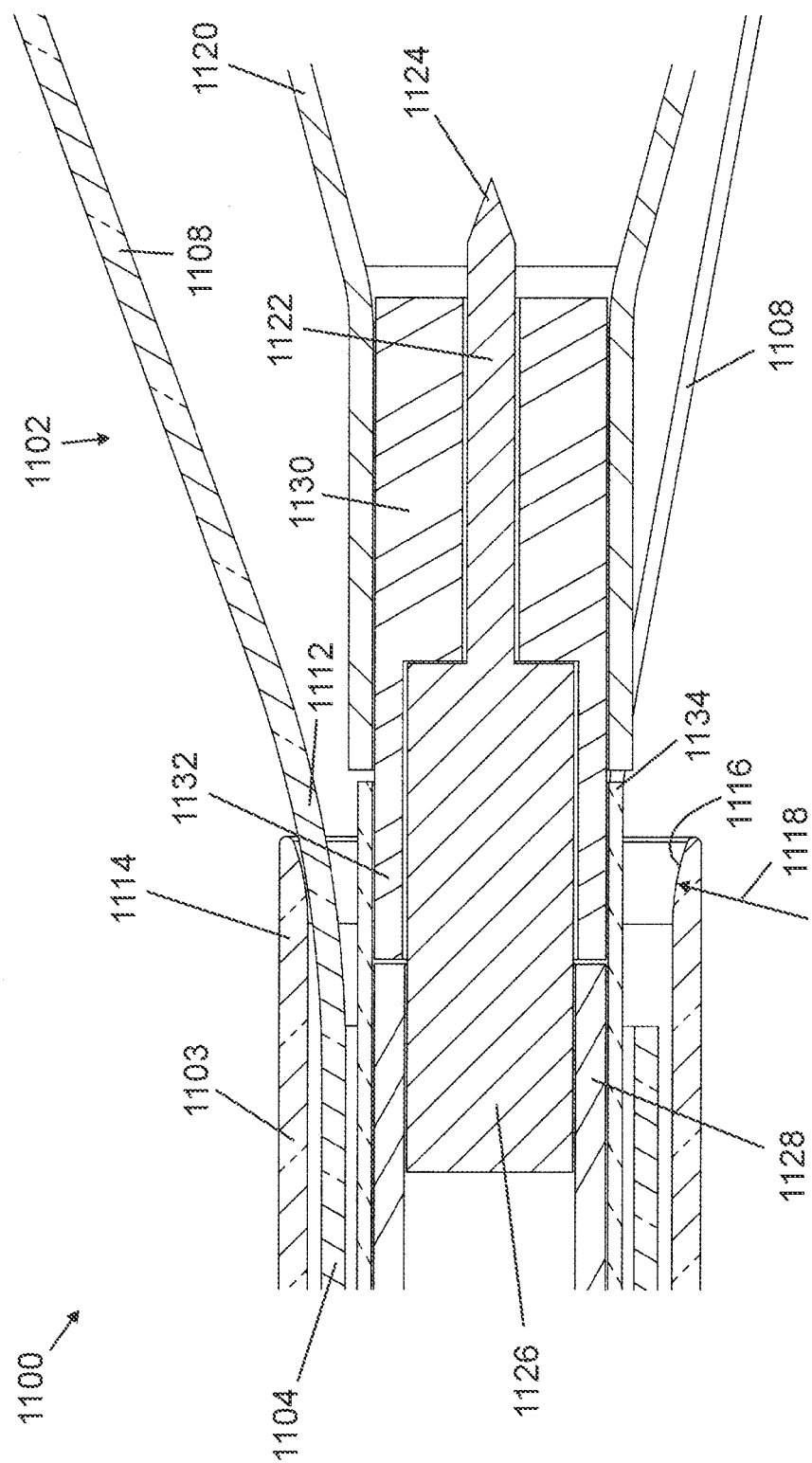
FIG. 43 is an expanded side sectional elevational view of the mid-portion of the objects of FIG. 41 as depicted in FIG. 42.
Figure 44:
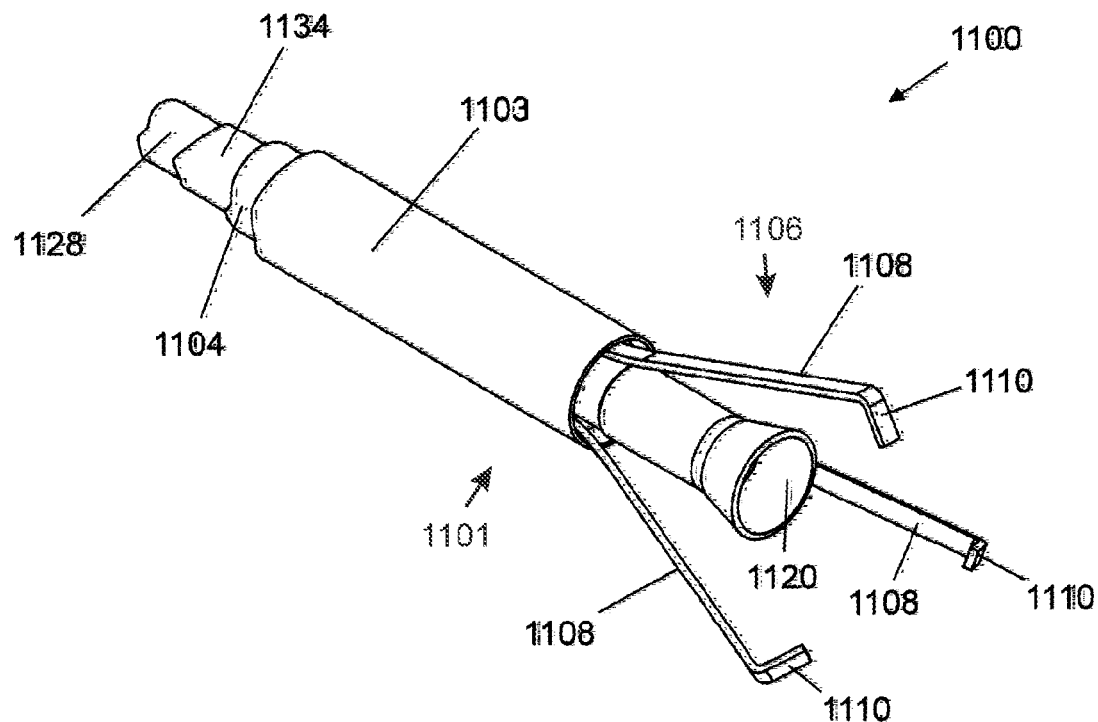
FIG. 44 is a perspective view of the objects of FIG. 41.
Figure 45:
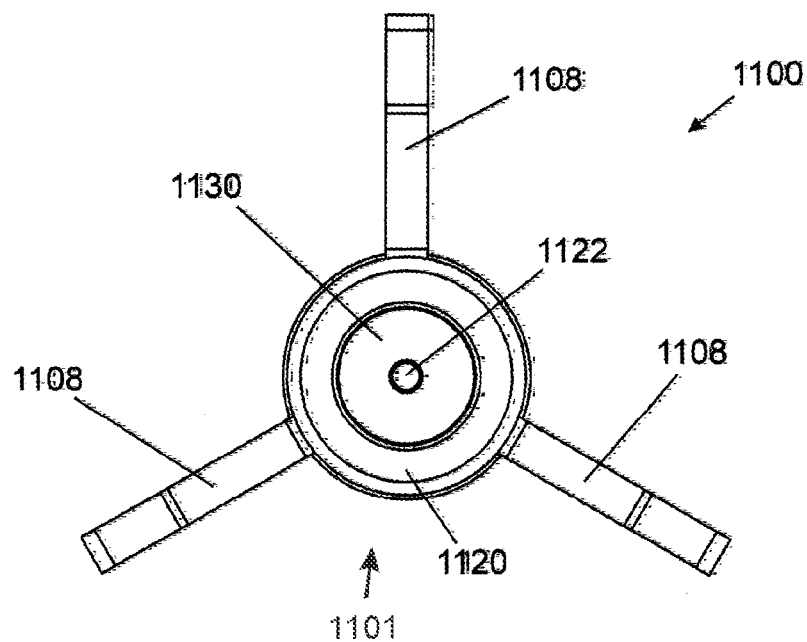
FIG. 45 is an expanded distal end view of the objects of FIG. 41.

Referring now to FIG. 40, depicting probe 900 in use eroding a kidney stone 990, a slight vacuum applied to opening 926 of active electrode 902 draws conductive liquid down the aspiration path and holds stone 990 in contact with or close proximity to the distal end of probe 900. Current (represented by arrows 980) flows from active electrode 902 to the conductive fluid and therefrom to a return electrode, the return electrode being either a dispersive pad (e.g., a monopolar application) or a return electrode on the probe (e.g., a bipolar application). A large portion of the current flows through floating electrode 912, entering in the distal portion 918 which is in close proximity to active electrode 902, and exiting in the portions of proximal portion 916 which are in lower potential portions of the electric field. High current density occurs in the conductive liquid in close proximity to both active electrode 902 and floating electrode 912. This causes rapid localized heating of the fluid, boiling of the fluid, and, when the bubbles formed reach a critical size, arcing within some of the bubbles. Some of the bubbles which intersect the active electrode and the surface of the stone, or which intersect the floating electrode and surface of the stone, support arcs 992 which affect the surface of the stone, vaporizing material in proximity to the arcs. This vaporization, along with fracturing of the stone caused by intense thermal gradients, creates debris which is aspirated from the site via lumen 922 of active electrode 902 and lumen 924 of tubular member 904. The process continues until stone 990 is sufficiently eroded for aspiration via probe 900 or other means.

In another embodiment configured for removal of kidney stones, a mechanism is provided for grasping a stone, and positioning and retaining it in proximity to the active and floating electrodes. Specifically FIGS. 41 through 45 depict the distal portion of probe 1100 having a subassembly 1101 for grasping stones slidably assembled thereto. Subassembly 1101 has a grasping element 1102 and a tubular control element 1103. Grasping element 1102 has a tubular proximal portion 1104 and a distal grasping portion 1106 having arms 1108. Arms 1108 have angled distal portions 1110 to aid in grasping a stone, and proximal portions 1112 formed to a radius and attached to the distal end of tubular proximal portion 1104 of element 1102. Tubular control element 1103 has at its distal end 1114 internal surface portion 1116 of radius 1118. Control element 1103 is slidably positioned on grasping element 1102 such that, when element 1103 is advanced distally relative to element 1102, surface 1116 acts on proximal portions 1112 of arms 1108 so as to deflect arms 1108 inwardly so as to grasp a stone in proximity to the distal end of probe 1100. When a stone has been grasped by arms 1108, subassembly 1101 (elements 1102 and 1103) is moved proximally until the stone is in contact with floating electrode 1120. Active electrode 1122 has a sharpened distal portion 1124 and a proximal portion 1126 which is assembled to conductive tubular member 1128. Insulator 1130 is assembled to active electrode 1122. Tubular member 1128 and proximal portion 1132 of insulator 1130 are covered with dielectric coating 1134.

Figure 46:
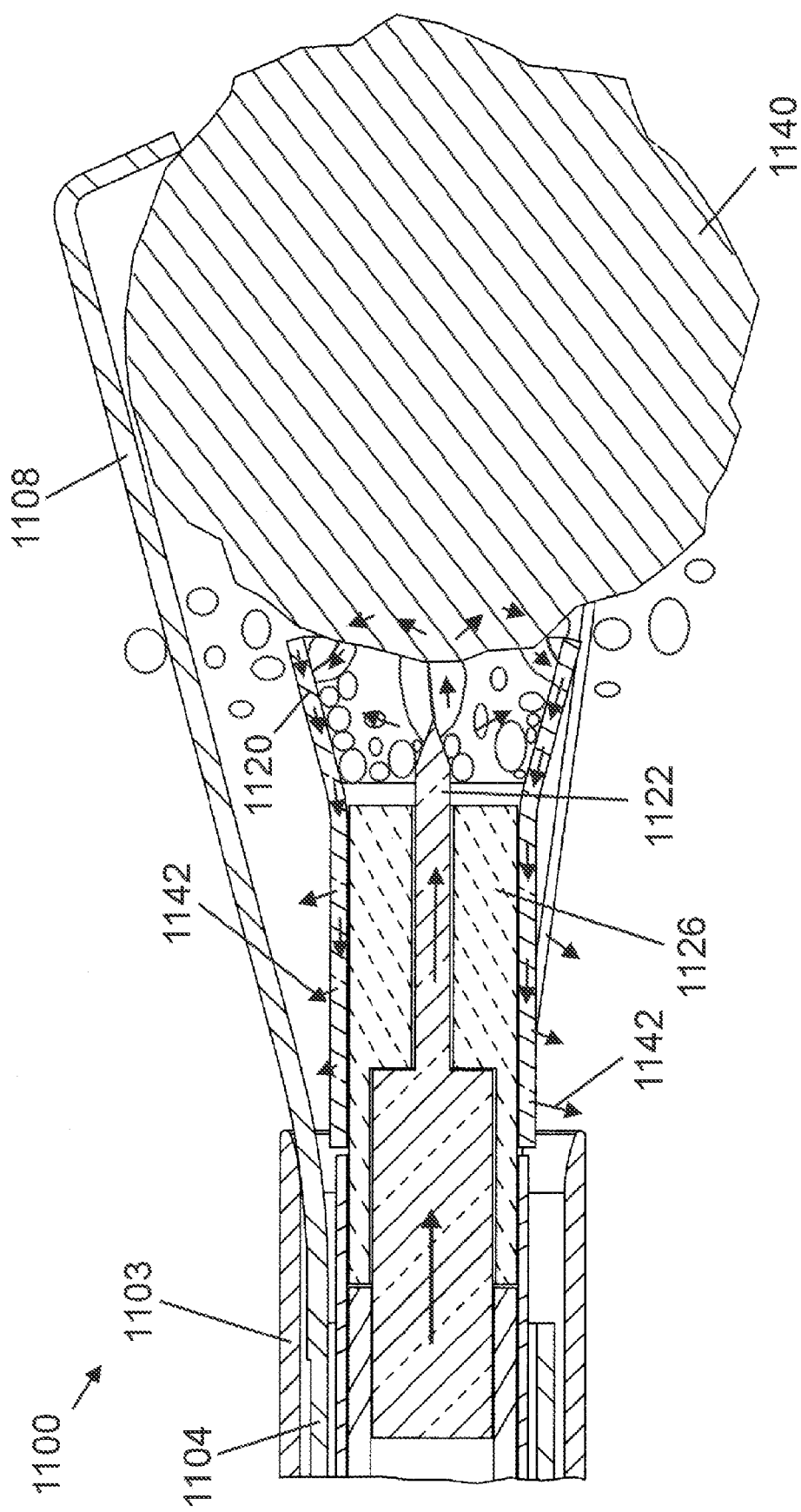
FIG. 46 is a side elevational sectional view of the objects of FIG. 41 during use.

Referring now to FIG. 46, which depicts probe 1100 in use, stone 1140 is positioned in close proximity to or contact with floating electrode 1120. Current (depicted by arrows 1142) flows from active electrode 1122 to a return electrode located at a remote location (e.g., a monopolar application) or on the instrument (e.g., a bipolar application). A portion of the current flows from active electrode 1122 to portions of floating electrode 1120 in close proximity to the active electrode, and then floating electrode 1120 via the surrounding conductive liquid to the return electrode. A portion of the current flowing to floating electrode 1120 flows through stone 1140. A portion of this current causes arcing at active electrode 1122 and/or arcing at floating electrode 1120, the arcing causing erosion and fracturing of stone 1140.

Figure 47:
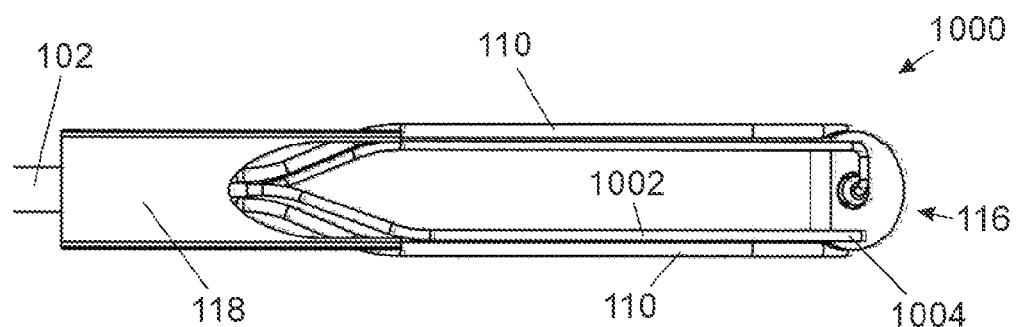
FIG. 47 is a plan view of an alternate embodiment having aspiration.
Figure 48:
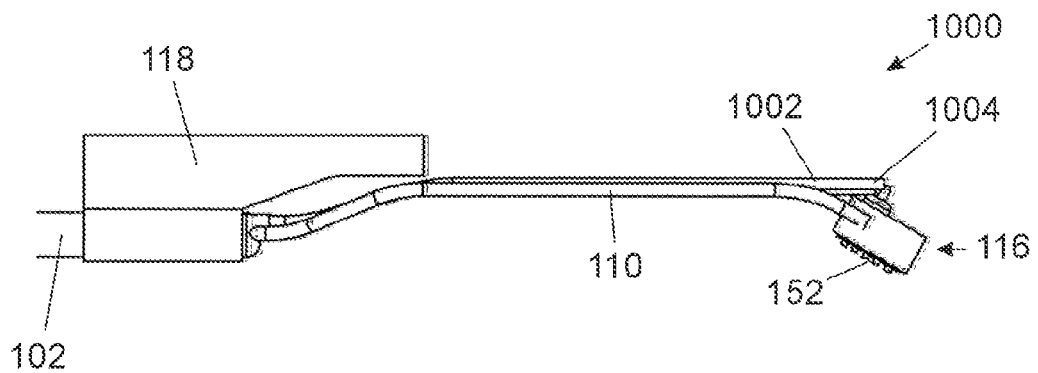
FIG. 48 is a side elevational view of the objects of FIG. 47.
Figure 49:
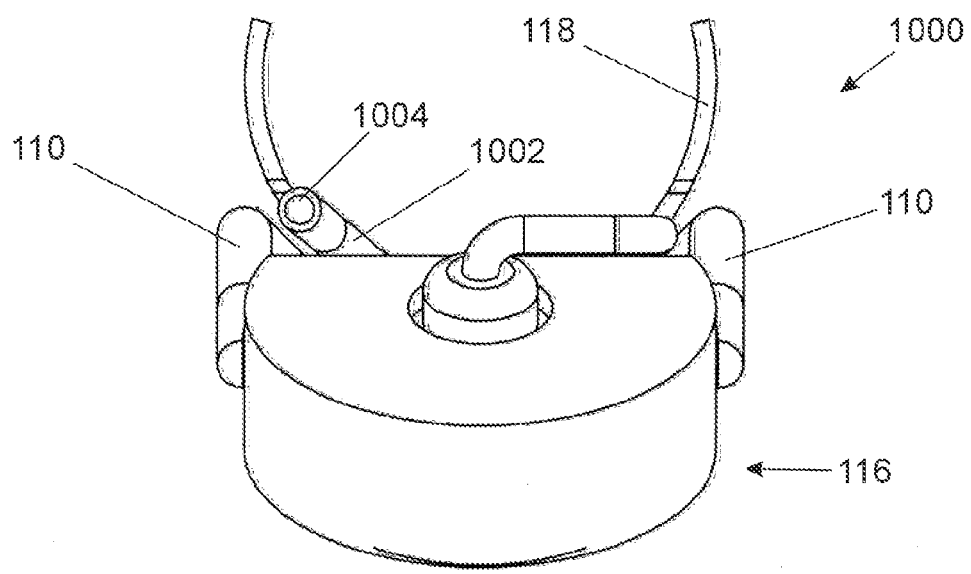
FIG. 49 is an expanded axial end view of the objects of FIG. 47.
Figure 50A:
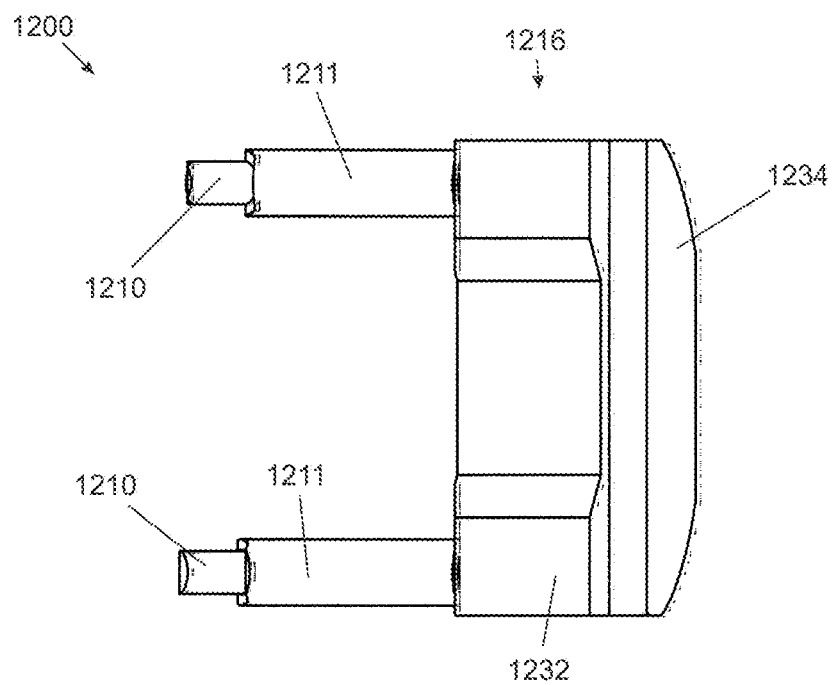
FIG. 50a is a plan view of the distal end electrode assembly of an alternate embodiment with simplified construction.

Aspiration may also be advantageous when vaporizing tissue. Bubbles formed during ablation of tissue may obscure the view of the surgeon and form pockets which displace conductive liquid from the surgical site. An electrosurgical probe formed in accordance with the principles of this invention and having ablation is depicted in FIGS. 47 through 49. Probe 1000 is constructed identically to probe 100 shown in FIGS. 1 through 9, but has added thereto aspiration tube 1002 which is in communication with an external vacuum source by means within tubular member 102. Distal end 1004 of tube 1002 is positioned on the back side of electrode assembly 116 so that liquid aspirated from the site contains only waste heat, rather than process heat as would be the case if distal end 1004 were in close proximity to active electrode 152.

Referring now to FIGS. 50a through 55, which depict the distal-most portion of probe 1200, referred to herein as the active head, electrode assembly 1216 includes active electrode 1230, insulator 1232 and floating electrode 1234. Active electrode 1230 has a plurality of grooves 1236 of width 1238 and depth 1240, width 1238 and depth 1240 being selected to trap bubbles in the grooves. Active electrode 1230 and floating electrode 1234 are preferably formed from a suitable metallic material, examples of which include, but are not limited to, such as stainless steel, nickel, titanium, tungsten, and the like. Insulator 1232 is preferably formed from a suitable dielectric material, example of which include, but are not limited to, alumina, zirconia, and high-temperature polymers. Members 1210, insulated by dielectric coating 1211, have affixed to distal ends 1214 of active electrode 1230 such that electrical power may be conducted by members 1210 to active electrode 1230. Members 1210 are connected by at least one conductive member of probe 1200 and external cabling to a suitable RF generator.

As with previously described embodiments, current flows from active electrode 1230 to the tissue or to the liquid environment, with a portion of the current flowing through floating electrode 1234. The current then flows to a return which may be a dispersive pad (not shown), or one or more return electrode 1280 located on the probe that are electrically connected to the electrosurgical generator (not shown). As with other embodiments, the current flow through the floating electrodes increases the current density in the portions of the field around the floating electrodes. This increased current density increases current flow at the active electrode thereby increasing the electrode efficiency.

Figure 51A:
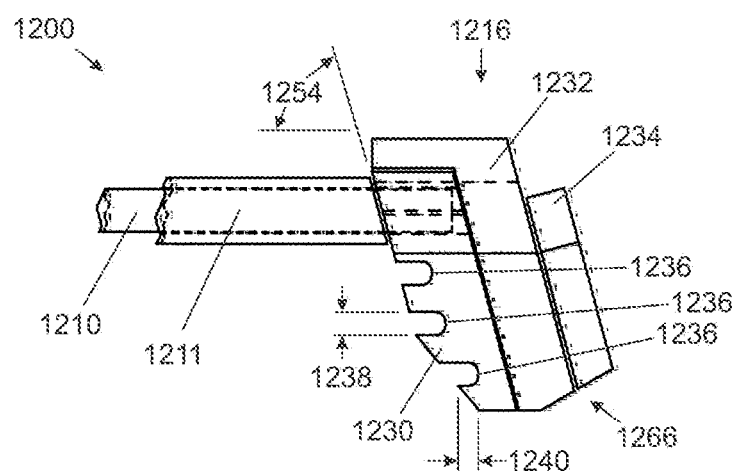
Figure 50B:
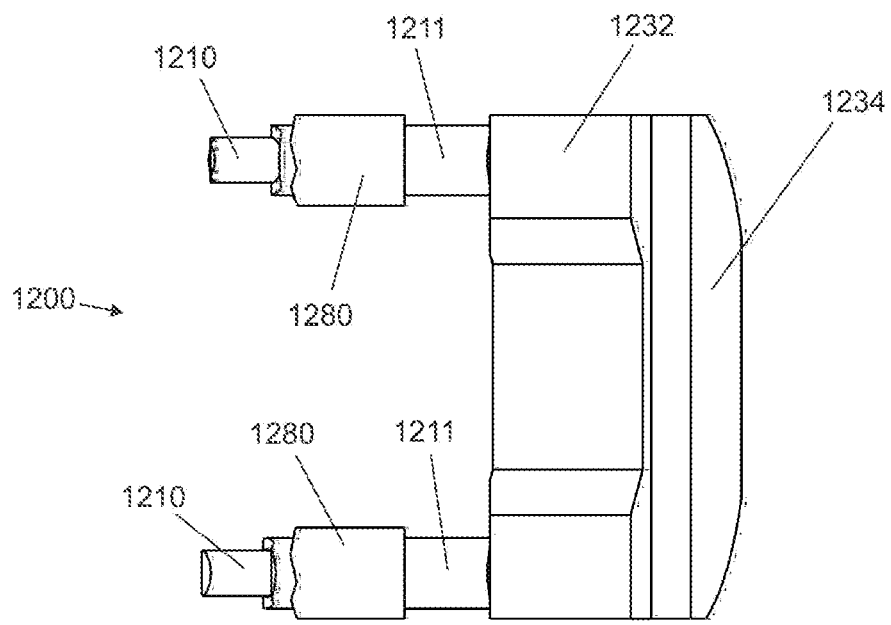
FIG. 50b is alternate view of embodiment depicted in FIG. 50a, with optional return electrodes (1280) included.
Figure 51B:
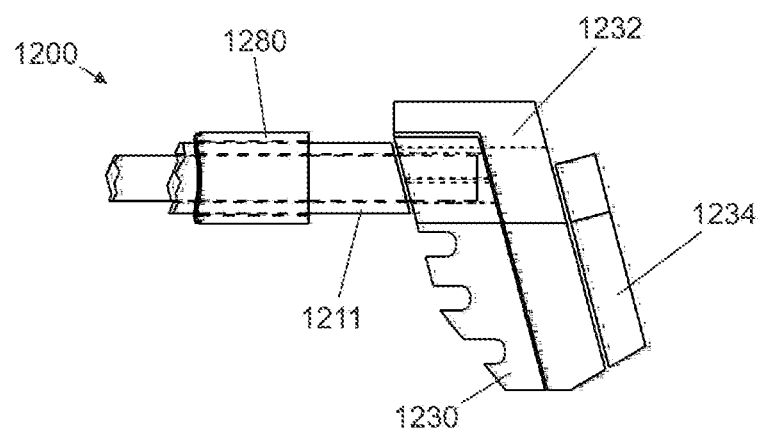
FIG. 51b is alternate view of embodiment depicted in FIG. 51a, with optional return electrode (1280) included.
Figure 52:
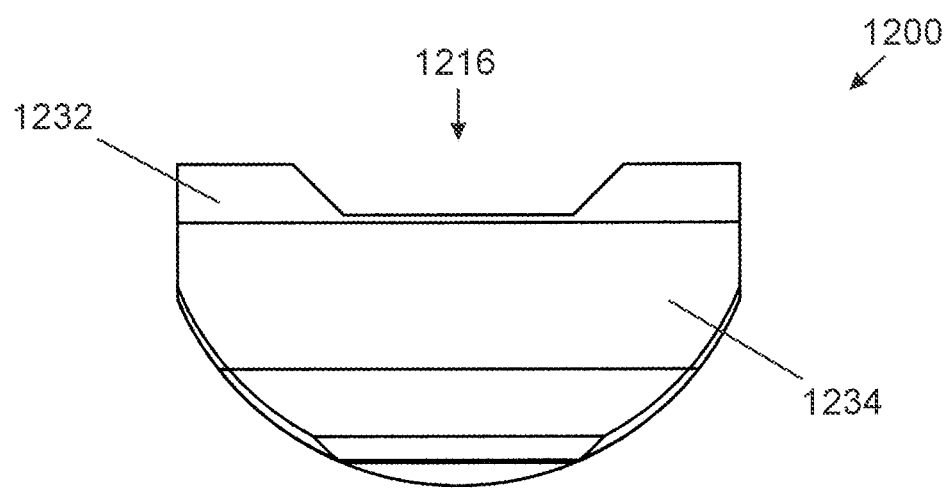
Figure 53:
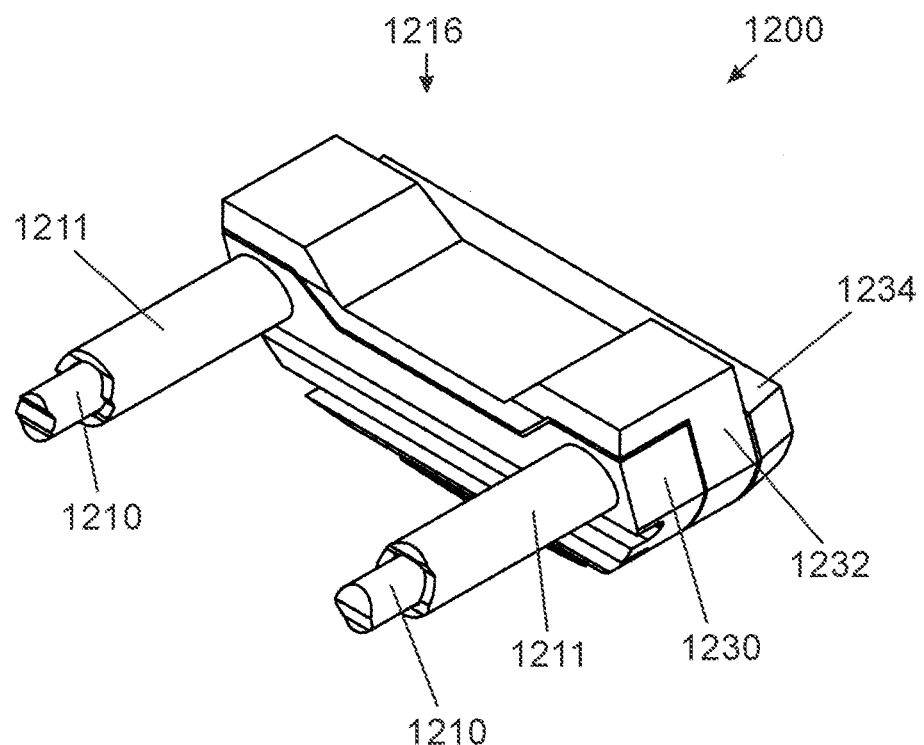
Figure 54:
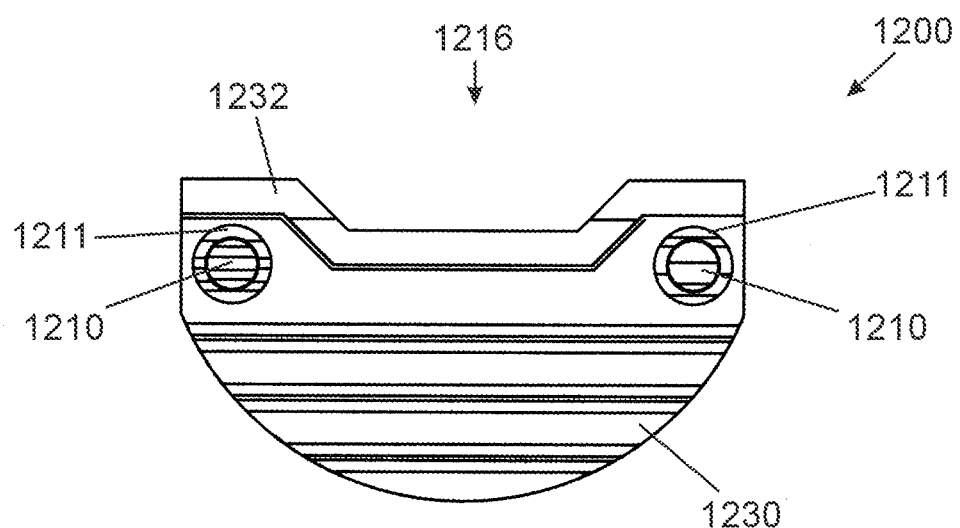
Figure 55:
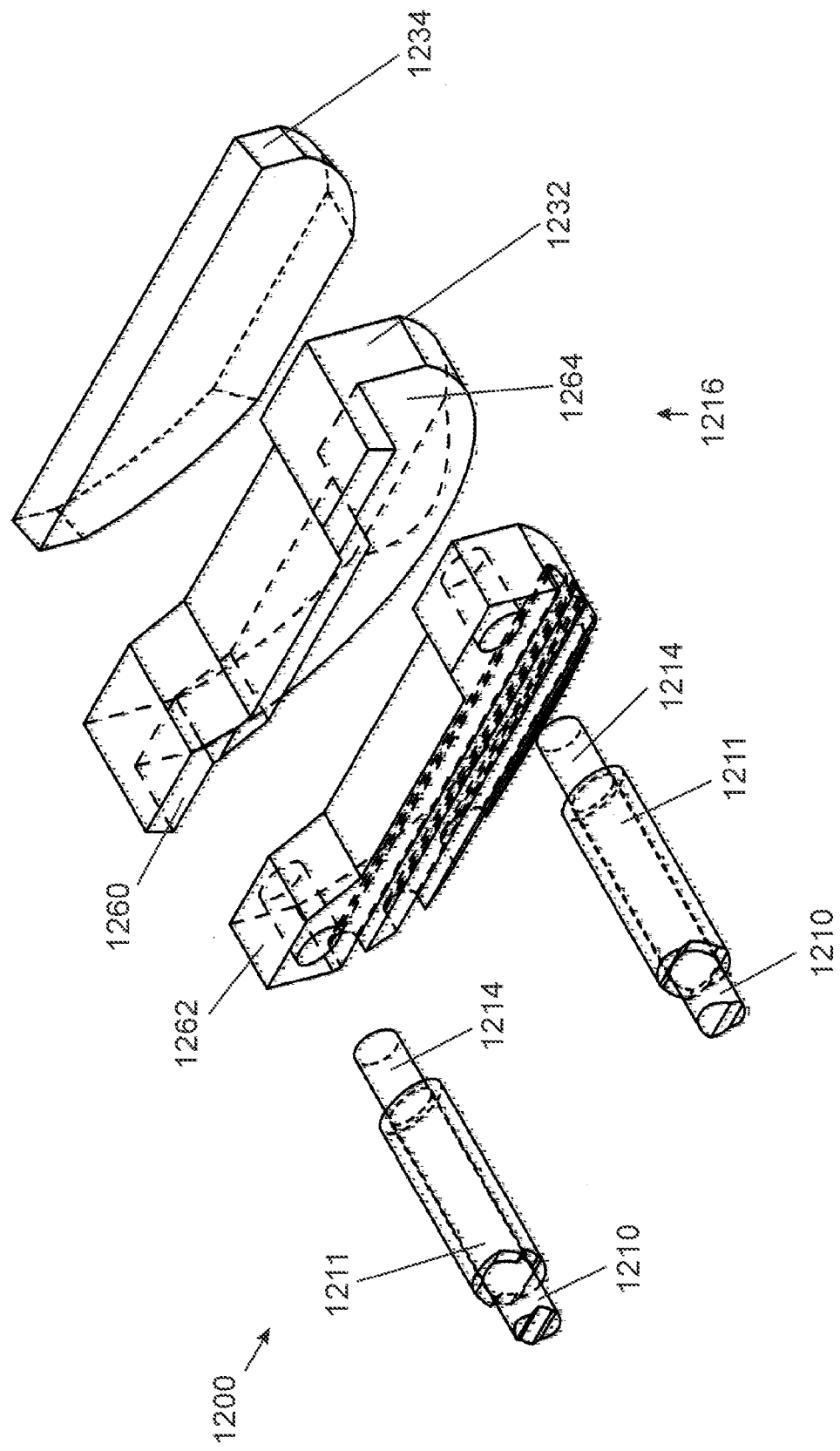

As best seen in FIG. 55, insulator 1232 has a first portion 1260 which insulates top surfaces 1262 of active electrode 1230, and a second portion 1264 which electrically isolates floating electrode 1234 from active electrode 1230. As best seen in FIG. 51, electrode assembly 1216 has a beveled lower portion 1266 formed on the lower distal portion of portion 1264 of insulator 1232 and the lower portion of floating electrode 1234. When viewed axially in the distal direction as in FIG. 54, floating electrode 1234 and second portion 1264 of insulator 1232 are flush with, or recessed behind active electrode 1230. Surface 1236 forms an acute angle 1254 with the axis of member 1210. Angle 1254 is preferably between 0 and 90 degrees, more preferably between 20 and 60 degrees.

Electrode assembly 1216 of probe 1200 has a simple construction which may be produced at low cost. Active electrode 1230 may be formed by machining using wire Electrical Discharge Machining and conventional machining, or by metal injection molding. Floating electrode 1234 may be stamped at low cost from sheet material. Insulator 1232 may be made by pressing and sintering, or by ceramic injection molding. Active electrode 1230 is joined to insulator 1232, and insulator 1232 is joined to floating electrode 1234 by a suitable biocompatible adhesive such as, for instance, EP62-1 MED or EP3HTMED epoxies by Master Bond Incorporated (Hackensack, N.J.) or Cement 31 by Sauereisen Incorporated (Pittsburgh, Pa.), all of which maintain their adhesive properties at the temperatures to which assembly 1216 may be heated during use. Alternatively, assembly 1216 may be held together by mechanical means, for example using fasteners such as screws, nuts, rivets or the like. Because members 1210 conduct power to active electrode 1230, it is not necessary to have a separate conductor such as conductor 126 of probe 100 (FIGS. 5 through 8), thereby further reducing the cost of probe 1200.

Probe 1200 is particularly useful for treating Benign Prostatic Hyperplasia (BPH), commonly referred to enlarged prostate. Surgical treatment of this condition is commonly accomplished using a resectoscope in a procedure referred to TransUrethral Resection of the Prostate (TURP). The resectoscope outer sheath is inserted into the urethra and the distal end advanced until it is near the prostate. The resectoscope working element with telescope and RF probe are inserted into the outer sheath such that the distal end of the probe can be used to modify or remove tissue. Most commonly, a cutting loop electrode (like that taught by Grossi et al in U.S. Pat. No. 4,917,082) is used to cut strips of tissue from the interior of the prostate, the site being filled with non-conductive irrigant. When sufficient tissue has been removed, the site including the bladder is flushed with irrigant to remove tissue strips that may remain at the site. The time required to flush the tissue from the site is frequently a significant portion of the total procedure time. Additionally, the use of non-conductive irrigant may lead to TUR syndrome, a potentially serious low blood sodium level. Gyms ACMI (Southboro, Mass.) has developed bipolar RF devices which operate in conductive irrigant. One of the products removes tissue by bulk vaporization so as to make removal of remaining tissue strips after resection unnecessary. Because the system is bipolar, its efficiency is low. As a result, high power levels are required to achieve acceptably high tissue removal rates. As noted previously, excessive power levels can lead to unintended injury to local tissue. The bipolar products are usable with conductive irrigants only.

Probe 1200 may be used to efficiently perform TURP procedures using either non-conductive or conductive irrigants. When non-conductive irrigant is introduced into the body, blood and other highly conductive bodily fluids contaminate the irrigant thereby making it conductive, the level of conductivity depending on the degree of contamination. When probe 1200 is submerged in an irrigant with any level of conductivity, floating electrode 1234 intensifies the electric field in close proximity to active electrode 1230 thereby increasing the current density and making conditions more favorable for tissue vaporization. This allows probe 1200 to be effectively used when either conductive or non-conductive irrigants are supplied to the site, the selection being based on surgeon preference.

Figure 56:
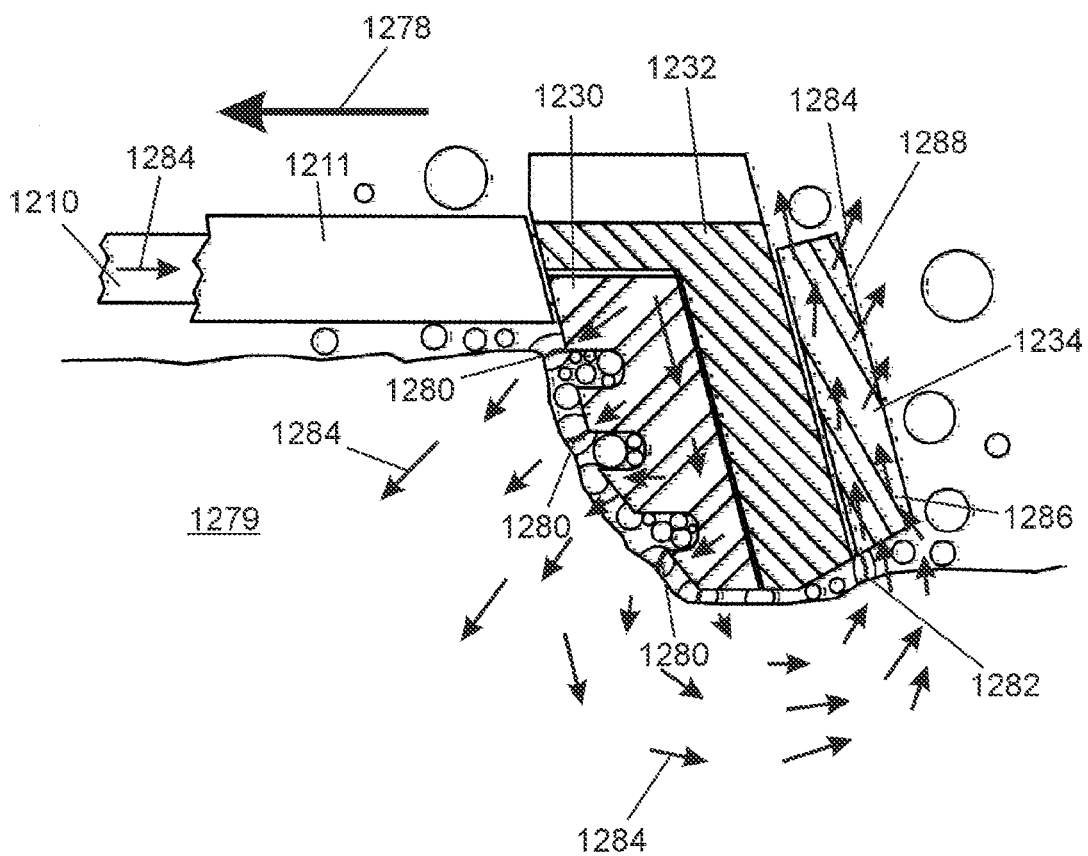
FIG. 56 is a sectional elevational side view of the probe of FIG. 50a during use.

Referring to FIG. 56 depicting probe 1200 in the context of a TURP procedure, probe 1200 is moved in a proximal direction 1278 relative to tissue 1279. Current (indicated by arrows 1284) from the RF generator, is supplied to active electrode 1230 by elements 1210. The current 1284 then flows from active electrode 1230 to a return electrode and therefrom to the generator. A portion of the current flows through tissue 1279 to tissue in close proximity to region 1286 of floating electrode 1234 in close proximity to active electrode 1230. This current flows through floating electrode 1234 to portion 1288 of floating electrode 1234 in a lower potential region of the electric field, and from floating electrode 1234 to the irrigant and therethrough to the return electrode. Some of the current flowing from active electrode 1230 to tissue 1279 causes boiling of irrigant in close proximity, arcing with the bubbles formed, and vaporization of tissue in the manner previously herein described. A portion of the current flow at region 1286 of floating electrode 1234 may have sufficient density to cause boiling, arcing and vaporization of tissue. A larger portion of the current flow has insufficient density to causing boiling of the irrigant, but does cause heating of the irrigant to elevated temperatures less than 100° C. The heated irrigant in these regions of lower current density causes thermal modification of adjacent tissue, specifically dessication of the tissue resulting in hemostasis.

When using probe 1200 to perform a TURP, a resectoscope sheath is introduced to the site in the standard manner. The working element with telescope and probe 1200 is inserted into the resectoscope sheath. Probe 1200 is extended distally past the end of the prostate slightly into the bladder. The distal end of the resectoscope is lowered somewhat such that when probe 1200 is energized and retracted proximally into the resectoscope, tissue intersected by active electrode assembly 1216 is vaporized so as to form a channel or groove in the prostate tissue. The scope position is adjusted and the process repeated to remove additional tissue. The process is repeated until the required volume of tissue is removed. Current flowing between active electrode 1230 and floating electrode 1234 thermally coagulates adjacent tissue thereby producing hemostasis.

All publications, patent applications, patents and other references mentioned herein are incorporated by reference in their entirety.

While the invention has been described in detail and with reference to specific embodiments thereof, it will be apparent to one skilled in the art that various changes and modifications can be made therein without departing from the spirit and scope of the invention.

What is claimed:

1. An electrosurgical instrument comprising:
   a. an elongate conductive shaft having a proximal end, a distal end and a longitudinal axis, wherein said proximal end is configured for connection to an electrosurgical power source;
   b. an electrode assembly mounted to the distal end of said elongate conductive shaft and comprising an active electrode, a floating electrode, and an insulator separating said active and floating electrodes, wherein:
      i. said insulator is disposed around said active electrode, and said floating electrode is disposed around said insulator;
      ii. said insulator is formed from a nonconductive dielectric material whereas said active and floating electrodes are formed from an electrically conductive material;
      iii. said active and floating electrodes are positioned in close proximity to each other;
      iv. said active electrode is electrically connected to said elongate conductive shaft whereas said floating electrode is not directly connected to either the elongate conductive shaft or the electrosurgical power source;
   c. a grasping subassembly slidably mounted proximate to said distal end of said elongate conductive shaft, said grasping subassembly comprising a plurality of grasping arms and a tubular control element positioned and axially slidable over said plurality of grasping arms, wherein advancement of said tubular control element in a distal direction causes said plurality of grasping arms to deflect inwardly and capture tissue retained therebetween.

2. The electrosurgical instrument of claim 1, each of said plurality of grasping arms comprises a radially projecting proximal portion assembled to an angled distal portion.

3. The electrosurgical instrument of claim 1, wherein said plurality of grasping arms comprises at least three grasping arms.

4. The electrosurgical instrument of claim 1, wherein said active electrode further comprises a sharpened distal tip.

5. The electrosurgical instrument of claim 1, wherein said floating electrode comprises a cylindrical proximal portion and a flared distal portion that extends distally past said active electrode.

6. The electrosurgical instrument of claim 1, wherein said electrosurgical instrument comprises a monopolar radiofrequency device.

7. The electrosurgical instrument of claim 1, wherein said electrosurgical instrument comprises a bipolar radiofrequency device.

8. The electrosurgical instrument of claim 7, wherein said bipolar radiofrequency device further comprises a return electrode mounted to said elongate conductive shaft.

9. A method of removing an obstruction comprising the steps of:
   A. introducing an electrosurgical instrument into a biological vessel or organ of a patient containing the obstruction, the electrosurgical instrument comprising:
      a. an elongate conductive shaft having a proximal end, a distal end and a longitudinal axis, wherein said proximal end is configured for connection to an electrosurgical power;
      b. an electrode assembly mounted to the distal end of said elongate conductive shaft and comprising an active electrode, a floating electrode, and an insulator separating said active and floating electrodes, wherein:
         i. said insulator is disposed around said active electrode, and said floating electrode is disposed around said insulator;
         ii. said insulator is formed from a nonconductive dielectric material whereas said active and floating electrodes are formed from an electrically conductive material;
         iii. said active and floating electrodes are positioned in close proximity to each other;
         iv. said active electrode is electrically connected to said elongate conductive shaft whereas said floating electrode is not directly connected to either the elongate conductive shaft or the electrosurgical power source;
c. a grasping subassembly slidably mounted proximate to said distal end of said elongate conductive shaft, said grasping subassembly comprising a plurality of grasping arms and a tubular control element positioned and axially slidable over said plurality of grasping arms, wherein advancement of said tubular control element in a distal direction causes said plurality of grasping arms to deflect inwardly and capture tissue retained therebetween;
B. manipulating the electrosurgical instrument such that the distal end of said elongate conductive shaft is proximate to said obstruction;
C. advancing the tubular control element in a distal direction relative to said plurality of grasping arms so as to deflect said plurality of grasping arms inwardly and capture said obstruction therebetween;
D. retracting the grasping subassembly in a proximal direction until the obstruction is in contact with or in close proximity to said floating electrode; and
E. applying a high frequency energy to said active electrode to generate regions of high current density, arcing and thermal gradients that vaporize and fracture the obstruction into smaller particles.

* * * * *

UNITED STATES PATENT AND TRADEMARK OFFICE
CERTIFICATE OF CORRECTION

PATENT NO. : 8,790,340 B2  
APPLICATION NO. : 13/493975  
DATED : July 29, 2014  
INVENTOR(S) : Robert Van Wyk et al.

Page 1 of 1

It is certified that error appears in the above-identified patent and that said Letters Patent is hereby corrected as shown below:

In the Claims

In claim 9, at column 22, line 51, insert the word --source-- after the word "power".

Signed and Sealed this
Sixteenth Day of December, 2014

Michelle K. Lee
*Deputy Director of the United States Patent and Trademark Office*